US008110606B2

(12) United States Patent
Kowalski et al.

(10) Patent No.: US 8,110,606 B2
(45) Date of Patent: *Feb. 7, 2012

(54) METHOD OF TREATING POST-SURGICAL ACUTE PAIN

(75) Inventors: Mark M. Kowalski, Winchester, MA (US); James L. Young, Valley Park, MO (US); Keith A. Moore, Loveland, OH (US)

(73) Assignee: Aaipharma Services Corp., Wilmington, NC (US)

( * ) Notice: Subject to any disclaimer, the term of this patent is extended or adjusted under 35 U.S.C. 154(b) by 186 days.

This patent is subject to a terminal disclaimer.

(21) Appl. No.: 12/706,117

(22) Filed: Feb. 16, 2010

(65) Prior Publication Data

US 2010/0144882 A1    Jun. 10, 2010

Related U.S. Application Data

(63) Continuation of application No. 12/391,434, filed on Feb. 24, 2009, now Pat. No. 7,662,858.

(60) Provisional application No. 61/055,581, filed on May 23, 2008.

(51) Int. Cl.
*A61K 31/195* (2006.01)

(52) U.S. Cl. ....................... 514/567; 424/451

(58) Field of Classification Search .................. None
See application file for complete search history.

(56) References Cited

U.S. PATENT DOCUMENTS

| | | | |
|---|---|---|---|
| 4,234,601 A | 11/1980 | Gardocki et al. |
| 4,948,581 A | 8/1990 | Sawayanagi et al. |
| 5,554,650 A | 9/1996 | Holl et al. |
| 5,854,226 A | 12/1998 | Penkler et al. |
| 6,214,838 B1 | 4/2001 | Sohda et al. |
| 6,287,594 B1 | 9/2001 | Wilson et al. |
| 6,365,180 B1 | 4/2002 | Meyer et al. |
| 6,419,954 B1 | 7/2002 | Chu et al. |
| 6,429,223 B1 | 8/2002 | Lai et al. |
| 6,869,615 B2 | 3/2005 | Chen et al. |
| 6,974,595 B1 | 12/2005 | Reiner et al. |
| 7,491,748 B2 | 2/2009 | Tani et al. |
| 7,572,776 B2 | 8/2009 | Yu et al. |
| 7,576,129 B2 | 8/2009 | Asada et al. |
| 7,662,858 B2 | 2/2010 | Kowalski et al. |
| 2005/0175608 A1 | 8/2005 | Tamura et al. |
| 2006/0122275 A1 | 6/2006 | Sakai et al. |
| 2007/0141182 A1 | 6/2007 | Niazi et al. |
| 2007/0197434 A1 | 8/2007 | Nakao et al. |
| 2009/0010986 A1 | 1/2009 | Ashton et al. |
| 2009/0292022 A1 | 11/2009 | Kowalski et al. |
| 2009/0292023 A1 | 11/2009 | Kowalski et al. |
| 2010/0010030 A1 | 1/2010 | Jain et al. |
| 2010/0222430 A1 | 9/2010 | Kowalski et al. |

FOREIGN PATENT DOCUMENTS

WO   WO 2006/017354   2/2006

OTHER PUBLICATIONS

Breivik, et al., "Assessment of Pain", *B. J. of Anesth.*, vol. 101, No. 1, pp. 17-24, (2008).
Breivik, et al. "Combining diclofenac with acetaminophen or acetaminophen-codeine after oral surgery: A randomized, double-blind single-dose study", Clin. Pharm. & Ther., vol. 66, No. 6, pp. 625- 635, (1999).
Cataflam® (diclofenac potassium immediate-release tablets) drug label, *Novartis*, pp. 1-16, revised (2009).
Cepeda, et al. "What decline in pain intensity is meaningful to patients with acute pain?", *Pain*, vol. 105, pp. 151-157, (2003).
Lasagna, et al., "Further Studies on the 'Pharmacology' of Placebo Administration", *J. Clin. Invest.*, vol. 37, No. 4, pp. 533-537, (1958).
Laska, et al., "The correlation between blood levels of ibuprofen and clinical analgesic response", *Clin. Pharmacol. & Ther.*, vol. 40, No. 1, pp. 1-7, (1986).
Lötsch, et al., "Population Pharmacokinetics of Fast Release Oral Diclofenac in Healthy Volunteers: Relation to Pharmacodynamics in an Experimental Pain Model", *Pharma. Res.*, vol. 17, No. 1, pp. 77-83, (2000).
Maciá, et al., "Comparative bioavailability of a dispersible formulation of diclofenac and finding of double plasma peaks", *Int'l J. of Clin. Pharma. and Therap.*, vol. 33, No. 6, pp. 333-339, (1995).
Millar, et al., "Practical Anaesthesia and Analgesia for Day Surgery," p. 160 (1997).
Mitchell, et al. "Selectivity of nonsteroidal anti-inflammatory drugs as inhibitors of constitutive and inducible" *Proc. Natl. Acad. Sci. USA*, vol. 90, pp. 11693-11697, (1994).
Riad, et al., "Effect of Food on the Multiple-Peak Behavior After a Single Oral Dose of Diclofenac Sodium Slow-Release Tablet in Humans", *Amer. J. of Therap.*, vol. 2, pp. 237-242, (1995).
Seymour, et al., "An evaluation of different ibuprofen preparations in the control of postoperative pain after third molar surgery", *B. J. Clin. Pharmacol*, vol. 31, pp. 83-87, (1991).
Standard of Care: "High Tibial Osteotomy," Brigham and Woman's Hospital, Department of Rehabilitation Services (2008).
Terhaag, et al., "Bioavailability of a new effervescent tablet of diclofenac" *Int'l J. of Clin. Pharm. and Therap.*, vol. 38, No. 11, pp. 546-551, (2000).
Zuniga, et al., "Controlled Phase III Clinical Trial of Diclofenac Potassium Liquid-Filled Soft Gelatin Capsule for Treatment of Post-operative Dental Pain," J Oral Maxillofac Surg, vol. 68(11), pp. 2735-2742 (2010).
Beck, et al., "Influence of diclofenac (group of nonsteroidal anti-inflammatory drugs) on fracture healing," *Arch. of Orthop. and Trauma Surg.*, vol. 123, No. 7, pp. 327-332, (2003), (Abstract Only).
Collins, et al., "Oral ibuprofen and diclofenac in post-operative pain: a quantitative systematic review," *Euro. J. of Pain*, vol. 2, pp. 285-291 (1998).

(Continued)

*Primary Examiner* — Brandon Fetterolf
*Assistant Examiner* — Craig Ricci
(74) *Attorney, Agent, or Firm* — McDonnell Boehnen Hulbert & Berghoff LLP

(57) ABSTRACT

A method is provided for treating pain in patients recovering from post-surgical trauma by administering between about 13 to about 30 mg of diclofenac potassium in a liquid dispersible formulation over a period of at least 24 hours, wherein the daily total amount of diclofenac potassium administered is less than or equal to about 100 mg. The method is particularly useful in treating acute pain in bunionectomy patients.

20 Claims, 2 Drawing Sheets

OTHER PUBLICATIONS

Desjardins, et al., "A randomized controlled study comparing rofecoxib, diclofenac sodium, and placebo in post-bunionectomy pain," *Current Medical Research and Opinions*, vol. 20, No. 10, pp. 1523-1537 (2004).

Hersh, et al., "Dose-Ranging Analegesic Study of ProSorb® Diclofenac Potassium in Postsurgical Dental Pain," *Clinical Therapeutics*, vol. 26, No. 8, pp. 1215-1227 (2004).

Hinz, et al., "Bioavailability of diclofenac potassium at low doses," *Brit. J. Clin. Pharma.*, vol. 59, No. 1, pp. 80-84 (2005).

Hofele, et al., "Efficacy and tolerability of diclofenac potassium sachets in acute postoperative dental pain: a placebo-controlled, randomized, comparative study vs. diclofenac potassium tablets," *Int. J. Clin. Pract.*, vol. 60, No. 3, pp. 300-307 (2006).

Krischak, et al., "Effects of diclofenac on periosteal callus maturation in osteotomy healing in an animal model," *J. Arch. Orthop. Trauma Surg.*, vol. 127, No. 1, pp. 3-9 (2007).

Marzo, et al., "Pharmacokinetics of Diclofenac after Oral Administration of its Potassium Salt in Sachet and Tablet Formulations," *Arzneim-Forsch./Drug Res.*, vol. 50, No. 1, pp. 43-47 (2000).

Moore, et al., "Pharmacokinetics of a novel liquid-gel formulation of diclofenac potassium," *The Journal of Pain*, vol. 9, No. 4, p. 33, Abstract No. 230 (2008).

Moore, et al., "Pharmacokinetics of a novel liquid-gel formulation of diclofenac potassium," May 2008 Poster presented at the 2008 American Pain Society (APS) 27th Annual Scientific Meeting, Tampa, Florida, USA.

Nelson, et al., "An Evaluation of the Analgesic Efficacy of Diclofenac Potassium, Aspirin, and Placebo in Postoperative Dental Pain," *Today's Ther. Trends*, vol. 12 (Supp. 1), pp. 3-14 (1994).

Reiner, et al., "Increased Absorption Rate of Disclofenac from Fast Acting Formulations Containing its Potassium Salt," *Arzneim-Forsch./Drug Res.*, vol. 51, pp. 885-890 (2001).

Schmidt, et al., "Analgesic Onset of a Novel Liquid Gel Formulation of Diclofenac Potassium in Post-Surgical Dental Pain," *The Journal of Pain*, No. 4, pp. 33, Abstract No. 231 (2008).

Schmidt, et al., "Analgesic Onset of a Novel Liquid Gel Formulation of DiclofenacPotassium in Post-Surgical Dental Pain," May 2008 Poster presented at the 2008 American Pain Society (APS) 27th Annual Scientific Meeting, Tampa, Florida, USA.

Tiseo, et al. "Experimental Study of the action of COX-2 selective nonsteroidal anti-inflammatory drugs and traditional anti-inflammatory drugs on bone regeneration," *Clinics*, vol. 61 (3), pp. 1-11 (online version) (Jun. 2006).

Tuzuner, et al., "Preoperative Diclofenac Sodium and Tramadol for Pain Relief after Bimaxillary Osteotomy,"*J. Oral Maxillofac. Surg.* pp. 2453-2458 (2007).

Zuniga, et al., "Analgesic Safety and Efficacy of Diclofenac Sodium Softgels on Postoperative Third Molar Extraction Pain", *J. Oral Maxillofac. Surg.*vol. 62, pp. 806-815 (2004).

Ahlström, et al., "The analgesic efficacy of diclofenac dispersible and ibuprofen in postoperative pain after dental extraction", *Eur. J. Clin. Pharm.*, vol. 44, pp. 587-588, (1993).

Bakshi, et al., "A Double-Blind, Placebo-Controlled Trial Comparing the Analgesic Efficacy of Two Formulations of Diclofenac in Postoperative Dental Pain", *Curr. Therap. Res.*, vol. 52, No. 3, (1992).

Bakshi, et al., "A Placebo-Controlled Comparative Evaluation of Diclofenac Dispersible Versus Ibuprofen in Postoperative Pain After Third Molar Surgery", *J. Clin. Pharm.*, vol. 34, pp. 225-230, (1994).

Daniels, et al. "Diclofenac Potassium Gelcap Significantly Reduced Moderate and Severe Post-bunionectomy Pain", American Society of Anesthesiologists Annual Meeting Abstracts, Abstract No. A795) Oct. 17-21, 2009, New Orleans, LA. (Abstract).

Daniels, et al., "Diclofenac Potassium Liquid Filled Capsules Significantly Reduced Moderate and Serve Post-bunionectomy Pain," Oct. 2009 Poster Presented at the 2009 Annual Meeting of the American Society of Anesthesiologists, New Orleans, Louisiana, USA.

Herbertson, "The Comparative Efficacy of Diclofenac Potassium, Aspirin, and Placebo in the Treatment of Patients with Pain Following Gynecologic Surgery", *Today's Ther. Trends*, vol. 12, pp. 33-45, (1994).

Kowalski et al., "A Pharmacokinetic Analysis of Diclofenac Potassium Soft-Gelatin Capsule in Patients After Bunionectomy", *American Journal of Therapeutics: Post Author Corrections*, (2009) (Abstract).

Mehlisch, et al., "Single-Dose Therapy with Diclofenac Potassium, Aspirin, or Placebo Following Dental Impaction Surgery", *Today's Ther. Trends*, vol. 12, pp. 15-31, (1994).

Derry, P. et al.: "Single dose oral diclofenac for acute postoperative pain in adults (Review)," The Cochrane Collaboration, published in The Cochrane Library 2009, Issue 3 (2009), pp. 1-57.

Riff et al. "Diclofenac potassium liquid-filled soft gelatin capsules in the management of patients with postbunionectomy pain: A phase III, multicenter, randomized, double-blind, placebo-controlled study conducted over 5 days", *Clinical Therapeutics*, vol. 31 (10), pp. 2072-2085, (2009) (Abstract).

Akritopoulos, et al., "Parecoxib has non-significant long-term effects on bone healing in rats when administered for a short period after fracture", *Arch. Orthop. Trauma Surg.*, vol. 129, pp. 1427-1432 (2009).

Aspenburg, "Per Avoid cox inhibitors after skeletal surgery!", *Acta. Orthop. Scand.*, vol. 73, No. 5, pp. 489-490 (2002).

Dumont, et al., "Nonsteroidal anti-inflammatory drugs and bone metabolism in spinal fusion surgery A pharmacological quandary", *J. of Pharmacol. and Toxicol. Methods*, vol. 43, pp. 31-39 (2000).

Forrest, et al., "Ketorolac, diclofenac, and ketoprofen are equally safe for pain relief after major surgery", *British J. of Anaesthesia*, vol. 88, No. 2, pp. 227-233 (2002).

Goodman, et al., "COX-2 selective NSAID decreases bone ingrowth in vivo", *J. of Orthop. Res.*, vol. 20, Issue 6, pp. 1164-1169, (2006) (Abstract).

Neal, et al., "A systematic survey of 13 randomized trials of nonsteroidal anti-inflammatory drugs for the prevention of heterotopic bone formation after major hip surgery", *Acta. Orthop. Scand.*, vol. 71, No. 2, pp. 122-128 (2000).

Waknine, "Diclofenac Liquid-Filled Capsules Approved for Pain Relief", Medscape Medical News > Alerts, Approvals and Safety Changes > FDA Approvals, (2009).

Weinbroum, et al., "Dextromethorphan-Associated Epidural Patient-Controlled Analgesia Provides Better Pain- and Analgesics-Sparing Effects than Dextromethorphan-Associated Intravenous Patient-Controlled Analgesia After Bone-Malignancy Resection: A Randomized, Placebo-Controlled, Double-Blinded Study", *Anesth. Analg.*, vol. 98, pp. 714-722 (2004).

Xanodyne Liquid Filled Capsules. URL: http://www.medicalnewstoday.com/articles/154377.php. (2009).

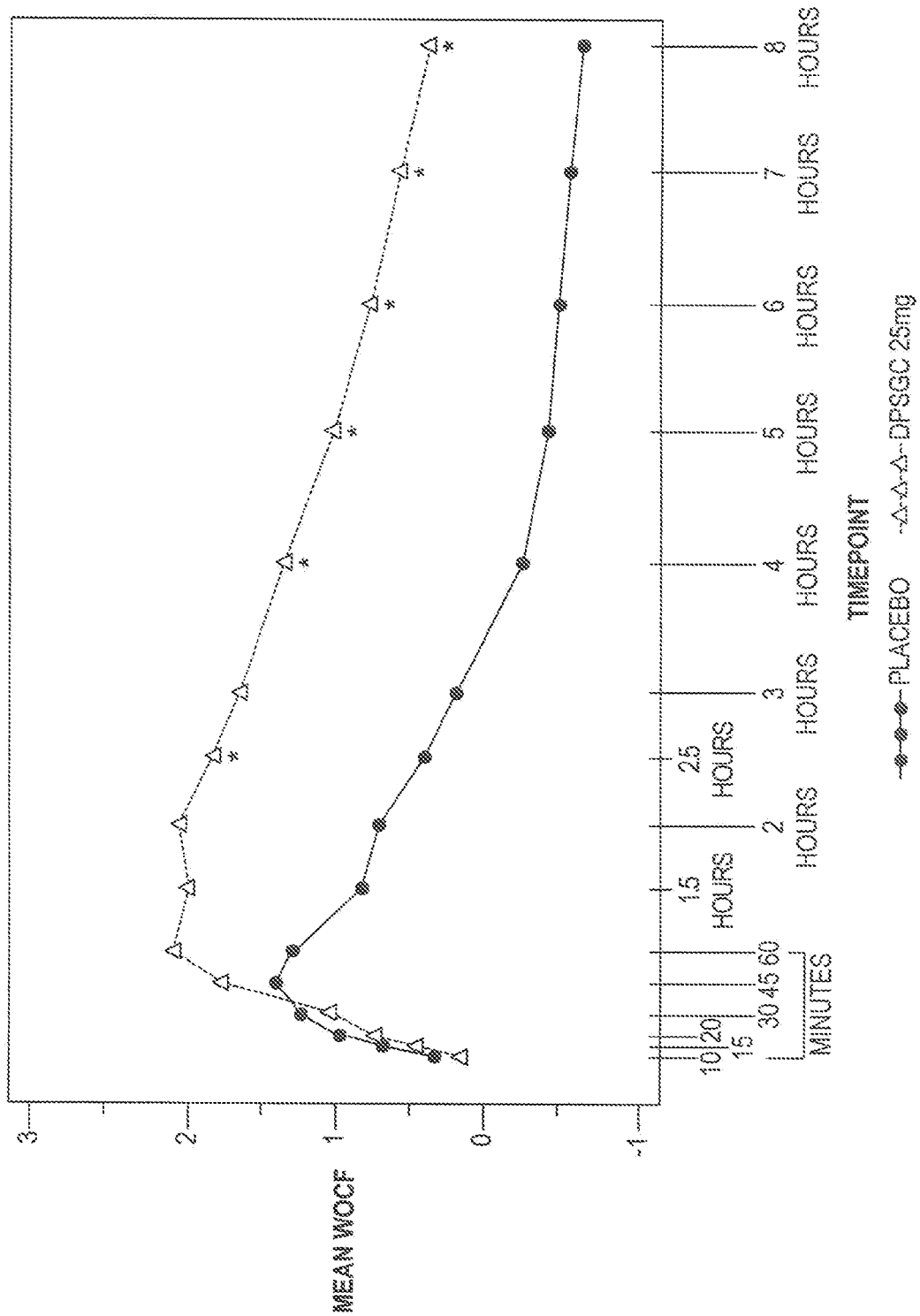

METHOD OF TREATING POST-SURGICAL ACUTE PAIN

CROSS-REFERENCE TO RELATED APPLICATION

This application is a continuation of U.S. application Ser. No. 12/391,434, filed Feb. 24, 2009, now U.S. Pat. No. 7,662,858, issued Feb. 16, 2010, which in turn claims the benefit of priority from U.S. Provisional application Ser. No. 61/055,581, filed May 23, 2008, which is hereby incorporated by reference in its entirety.

FIELD OF THE INVENTION

The present invention relates to a method for treating acute pain in a patient recovering from post-surgical trauma which employs an orally administered low dose amount of diclofenac potassium in a dispersible liquid formulation. Specifically, the present invention relates to a method for treating acute pain in patients recovering from a bunionectomy which utilizes an orally administered low dose amount of diclofenac potassium in a dispersible liquid formulation.

BACKGROUND OF THE INVENTION

Pain is an unpleasant sensory and emotional experience arising from actual or potential tissue damage. Pain is highly subjective to the individual experiencing it, but medical diagnosis is based on characterising it in various ways such as the duration, severity, type (dull, burning or stabbing), and location in body. Experiencing pain is influenced by a number of dynamic, changing and interacting physical, mental, biochemical, physiological, psychological, social, cultural and emotional factors. Thus, pain perceived as intense at one time may at another time be perceived as less intense although all other factors appear to be constant.

Pain management divides symptoms into acute or chronic pain. Acute pain is distinguished from chronic pain. Acute pain warns the patient that something is wrong, and may result from a variety of causes including tissue damage, infection and/or inflammation. Chronic pain, on the other hand, may have no apparent cause or may be caused by a developing illness or imbalance. Sometimes chronic pain can have a psychosomatic or psychogenic cause.

Surgical procedures often result in some form of acute pain. Surgical pain may include nociceptive, neuropathic or psychological components. Nociceptive pain is a pain experienced as a result of nociception, which is detection of a stimulus by a pain receptor (nociceptor) and transmission of the information to the brain along nerves. Nociceptive pain is caused by tissue damage and inflammation in response to trauma. The resulting pain is usually not well localized and is opioid responsive.

The goal of post-surgical pain management is twofold: i) to provide a quick onset of analgesic or pain relief and ii) to reduce or modulate the quality and intensity of pain a patient experiences in the post-surgical period. The improvement in minimally invasive surgical techniques has resulted in a reduction in patient time in a hospital and has shifted many procedures to the physician's office. Outpatient surgery has become a procedure of choice for many simple to complex procedures, such as bunionectomy, knee surgery, hernia repair, tonsillectomy, carpel tunnel release, cataract removal, hysterectomy and prostatectomy. The patient must now be made comfortable enough in a short period of time to return home and safely manage his or her own pain. Medications that provide gradual but extended response to acute pain situation are often inappropriate in this situation.

Treatment for acute pain after bunionectomy surgery typically consists of opioid and/or NSAIDs/COX-2 inhibitors. In some cases, opioids are given for several days and then the subject is treated with an NSAID or COX-2 Inhibitor. However, interest in the cardiovascular risk associated with the use of COX-2 inhibitors has become intense, especially in regard to rofecoxib and celecoxib. While current treatments for management of post-surgical acute pain are useful, there is a need for improved methods for treating post-surgical acute pain, particularly following bunionectomy, which provides immediate relief of acute pain with little or no risk of a cardiovascular event.

BRIEF DESCRIPTION OF THE DRAWINGS

FIG. 2 depicts Day 1 mean PID scores over time (Full Analysis Population)

SUMMARY OF THE INVENTION

Figure 1:
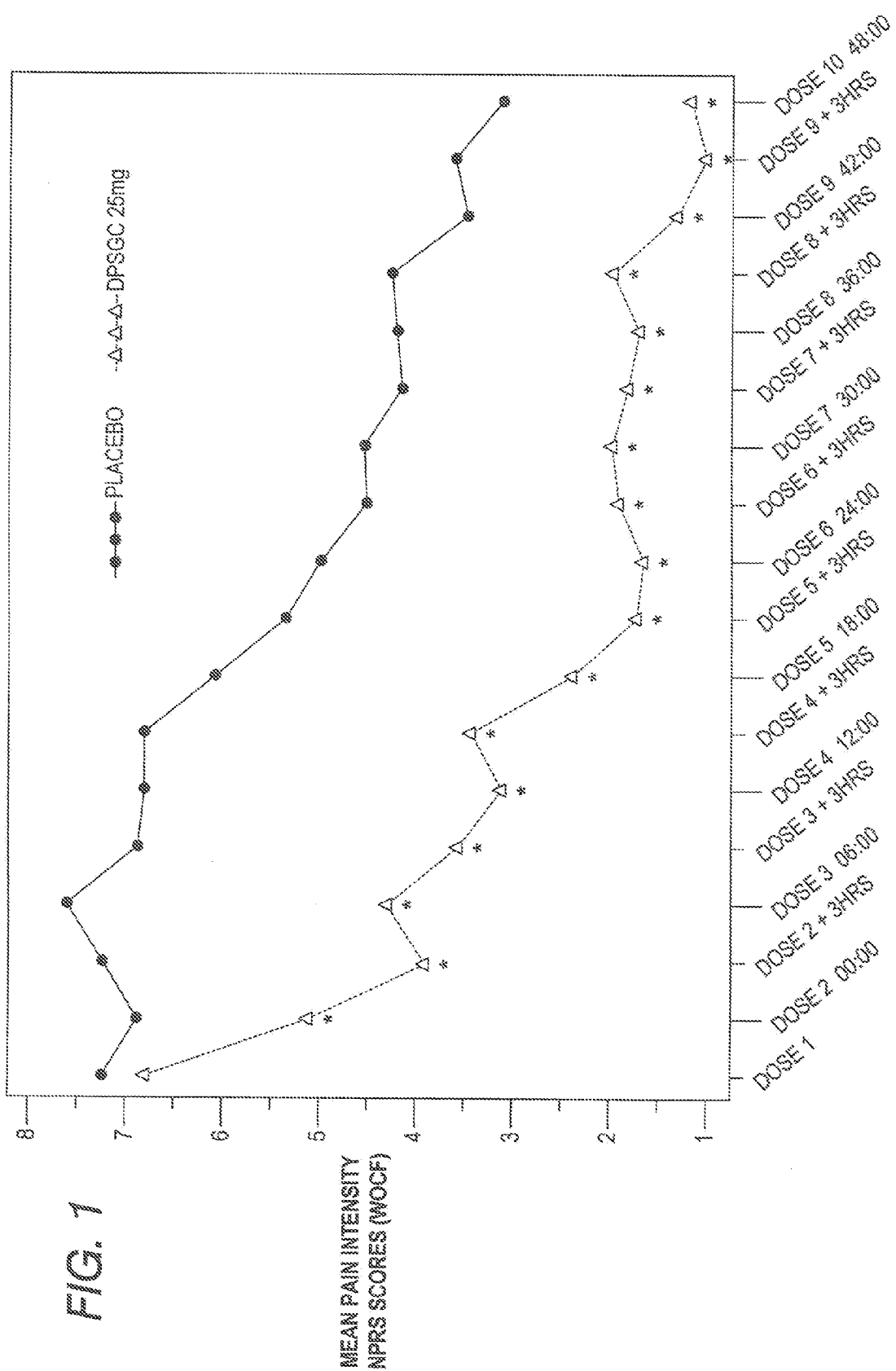
FIG. 1 depicts mean NPRS pain intensity scores over time during the 48-hour multiple dose period (Full Analysis Population)

In a first aspect, the invention provides a method of treating acute post-surgical pain, e.g., osteotomy pain, in a patient in need of such treatment, said method comprising the step of orally administering to the patient a dose of between about 13 to about 30 mg of diclofenac potassium in an liquid dispersible formulation every 4 hours to 8 hours over a period of at least 24 hours, wherein the daily total amount of diclofenac potassium administered is less than or equal to about 100 mg.

In one embodiment of the first aspect, the pain results from a bunionectomy.

In another embodiment of the first aspect, internal fixation may be performed during the bunionectomy.

In a second aspect, the invention provides a method of treating acute post-bunionectomy pain in a patient in need of such treatment, said method comprising orally administering to the patient a dose of between about 13 to about 30 mg of diclofenac potassium in a dispersible liquid formulation every 4 hours to 8 hours over a period of at least 24 hours, wherein the daily total amount of diclofenac potassium administered is less than or equal to about 100 mg.

In one embodiment of the second aspect, internal fixation may be performed during the bunionectomy.

In one embodiment of either aspect, the diclofenac potassium in the dispersible liquid formulation is administered about every 5 hours to about 8 hours.

In another embodiment of either aspect, the diclofenac potassium in the dispersible liquid formulation is administered about every 6 hours.

In another embodiment of either aspect, the diclofenac potassium in the dispersible liquid formulation is administered over a period of at least about 30 hours.

In another embodiment of either aspect, the diclofenac potassium in the dispersible liquid formulation is administered over a period of at least about 48 hours, 72 hours, 96 hours, 120 hours, 144 hours, 168 hours or seven days.

In another embodiment of either aspect, the amount of the diclofenac potassium in the dispersible liquid formulation comprises at least about 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 22.5 mg, 25 mg, 27.5 mg, 28 mg, or 30 mg of diclofenac potassium.

In another embodiment of either aspect, the administered amount of diclofenac potassium in the dispersible liquid formulation is effective for treating the pain for about 6 to about 8 hours after administration.

In another embodiment of either aspect, the plasma concentration of diclofenac in a patient ranges between about 670 to about 1500 ng/ml in less than 30 minutes with the concomitant onset of relief of acute pain.

In another embodiment of either aspect, the administration of diclofenac potassium in the dispersible liquid formulation results in immediate increase in plasma concentration of diclofenac characterized by T(max) of 0.47 hours.

In another embodiment of either aspect, diclofenac is substantially eliminated from plasma in the first 2 hours following administration.

In another embodiment of either aspect, the amount of the diclofenac potassium in the dispersible liquid formulation comprises about 25 mg of diclofenac potassium.

In another embodiment of either aspect, the administration of diclofenac potassium in the dispersible liquid formulation results in an average 48 hour NPRS pain score of about 2.49.

In another embodiment of either aspect, the administration of diclofenac potassium in the dispersible liquid formulation results in a median time to onset of greater than or equal to 30% pain reduction of about 60 minutes in a 6 to 8 hour initial dosing period.

In another embodiment of either aspect, the administration of diclofenac potassium in the dispersible liquid formulation provides a median time to onset of meaningful pain relief of about 70 minutes in a 6 to 8 hour initial dosing period.

In another embodiment of either aspect, the administration of diclofenac potassium in the dispersible liquid formulation provides clinically significant analgesic efficacy for about 6 hours.

In another embodiment of either aspect, 25 mg of diclofenac potassium in the dispersible liquid formulation is administered four times over a period of about 24 hours.

In another embodiment of either aspect, the diclofenac potassium in the dispersible liquid formulation is contained in a capsule such as a soft or hard gelatin capsule.

In another embodiment of either aspect, no opioid is co-administered with the diclofenac potassium in the dispersible liquid formulation.

In another embodiment of either aspect, the acute pain comprises mild to moderate pain, moderate to moderately severe pain, or moderate to severe pain.

These and other embodiments of the invention will become apparent in light of the detailed description below.

DETAILED DESCRIPTION OF THE INVENTION

The present invention provides a method for treating acute pain in patients recovering from post-surgical trauma such as that resulting from osteotomy. The method is particularly useful in treating acute pain in patients that have undergone outpatient surgical procedures such as bunionectomy. The method comprises orally administering between about 13 to about 30 mg, e.g., about 25 mg, of diclofenac potassium in a dispersible liquid formulation about every four hours to 8 hours for a period of at least 24 hours, wherein the daily total amount of diclofenac potassium administered is less than or equal to about 100 mg.

The method is based on the surprising discovery that post-surgical analgesia, particularly post-osteotomy analgesia, can be achieved, without the need for opioids, with a relatively low oral dose (e.g., between about 13 mg to about 30 mg) of diclofenac potassium in a dispersible liquid formulation. Surgical procedures, such as bunionectomy, that are typically performed as an outpatient procedure have a preferential need for post-surgical analgesic methods that can be administered without substantial patient overview. Consequently, use of analgesics that affect, inter alia, motor functions, such as opioids, are not desirable for management of post-surgical pain after an outpatient surgical procedure. The post-surgical analgesia achieved with a low oral dose dispersant liquid diclofenac potassium preparation provides sufficient analgesia to delay or suspend the use of an opioid in the treatment of acute post-surgical pain, and is, therefore, an effective method of pain management after an outpatient surgical procedure. The method of the invention surprisingly provided effective pain relief for patients who had undergone osteotomy, e.g., bunionectomy surgery, without an increased risk of a treatment related adverse event relative to the control.

All publications, patent applications, patents and other references mentioned herein, if not otherwise indicated, are explicitly incorporated by reference herein in their entirety for all purposes as if fully set forth.

Unless otherwise defined, all technical and scientific terms used herein have the same meaning as commonly understood by one of ordinary skill in the art to which this invention belongs. In case of conflict, the present specification, including definitions, will control.

Except where expressly noted, trademarks are shown in upper case.

Unless stated otherwise, all percentages, parts, ratios, etc., are by weight.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present invention be limited to the specific values recited when defining a range.

When the term "about" is used in describing a value or an end-point of a range, the invention should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the invention. This description should be read to include one or at least one and the singular also includes the plural unless it is obvious that it is meant otherwise.

Diclofenac Potassium in a Dispersible Liquid Formulation:

The present invention relates to a method for treating acute pain such as that resulting from an osteotomy, e.g., a bunionectomy, based on use of an oral dispersible liquid formulation comprising diclofenac potassium and at least one pharmaceutically acceptable, non-toxic dispersing agent. A particularly useful dispersible liquid formulation of diclofenac potassium is described in U.S. Pat. No. 6,365,180, which is hereby incorporated by reference in its entirety. Another useful orally administered dispersible liquid formulation of diclofenac potassium, based on the use of a bicarbonate dispersing agent, is described in U.S. Pat. No. 6,974,595 (i.e., Examples 6 and 7), which is incorporated by reference in its entirety. Diclofenac (potassium [2-(2,6-dichlorophenyl)amino]-phenyl]acetate), is a potent nonsteroidal anti-inflammatory (NASID) drug therapeutically used in inflammatory conditions and as an analgesic. Like other NASIDs, diclofenac interacts with the arachidonic acid cascade at the level of cyclo-oxygenase. Diclofenac inhibits cyclo-oxygenase at micromolar concentrations and as a consequence the formation of thromboxanes, prostaglandins and prostacyclin is inhibited under various clinical and experimental conditions. As used herein, the term "pharmaceutically acceptable," when referring to any or all components of the present compositions, means that such component(s) are compatible with other components therein, and not deleterious to the recipient thereof.

A dispersing agent is a surface-active substance added to a suspension, usually a colloid, to improve the separation of particles and to prevent settling or clumping in the gastrointestinal tract by facilitating distribution of particles or droplets throughout the gastrointestinal tract. Any pharmaceutically acceptable dispersing agents may be used, including, for example, alkali metal bicarbonates or mixtures thereof, such as potassium bicarbonate in amount 20-80% by weight of the weight of diclofenac; the polymer-based dispersing agents which include, for example, polyvinylpyrrolidone (PVP; commercially known as Plasdone™); and the carbohydrate-based dispersing agents such as, for example, hydroxypropylmethylcellulose (HPMC), hydroxypropylcellulose (HPC), and the cyclodextrins. Useful dispersing agents include PVP K29-32, dextrins, starch, derivatized starch and dextrans, while of the dextrins, derivatized cyclodextrins are especially useful. Of such cyclodextrins, hydroxypropyl beta-cyclodextrin and gamma-cyclodextrin are especially preferred. The numbers relate to the molecular weight of the polymer wherein, for example, PVP K-30 has an average molecular weight of about 30,000, with attendant viscosity characteristics.

The dispersible liquid formulation further comprises at least one pharmaceutically acceptable non-toxic solubilizing agent. Such readily available solubilizing agents are well known in the art and is typically represented by the family of compounds known as polyethylene glycols (PEG) having molecular weights from about 200 to about 8,000. For liquid formulations used for filling soft capsules such as soft gelatin capsules, suitable molecular weights range from about 200 to about 600 with PEG 400 being especially useful. Another example of suitable solubilizing agent includes sorbitol.

Optionally, another solubilizing agent which may be utilized in compositions of the present invention is water, especially purified and deionized water. For such compositions, the concentration of water is from about zero percent to about ninety-nine percent (w/w). More particularly for compositions of the present invention to be filled into soft capsules, a maximum water concentration from about 0% to about 5% is preferred, although the concentration of total solubilizing agent may be the full concentration range taught herein.

As used in the present compositions, the concentration of the sum of solubilizing agent utilized, wherein more than one solubilizing agent can be utilized, is from about 0 percent to about 99 percent (w/w). The preferred concentration of solubilizing agent in the present compositions is from about 60 percent to about 90 percent (w/w).

If the dispersible liquid formulations are to be filled in soft gelatin capsules, is at least one optional pharmaceutically acceptable, non-toxic plasticizing agent may be used. Such plasticizing agents, which are well known in the pharmaceutical formulation art, include, for example, glycerin, propylene glycol, and sorbitol. Such commercially available plasticizers can be prepared to include more than one plasticizing agent component, but the preferred plasticizing agent for the present compositions is glycerin. In addition to its use as a plasticizing agent, propylene glycol can be used as a solubilizing agent when used alone or in combination with another solubilizing agent as taught herein.

As used in the present invention, the concentration of the sum of plasticizing agent utilized, wherein more than one plasticizing agent can be utilized, is from about zero percent to about 75 percent (w/w). The preferred of plasticizing agent is from about zero percent (0%) to about fifty percent (50%), and an especially preferred concentration in a range from about one percent (1%) to about thirty percent (30%). When the compositions of the present invention are used to fill soft gelatin capsules, the general concentration of such plasticizing agent ranges from about 5 percent to about 10 percent (w/w). Such plasticizers are especially useful with soft gelatin capsule preparations because, without which, such capsules tend to harden and lose their beneficial properties by, potentially, cracking or becoming brittle.

Another optional component of the present compositions, which is a preferred component, is at least one pharmaceutically acceptable, non-toxic, surfactant, preferably a non-ionic surfactant. Such surfactants are well known in the pharmaceutical formulation art and include readily available surfactants having a concentration from about zero percent to about 90 percent such as, for example, macro gel esters (Labrafils), Tandem 522™, Span 80™, Gelucieres™, such as, for example, tocopherol polyethylene glycol 1000 succinate, polysorbate 20, and polysorbate 80. Of these, polysorbate 20 and polysorbate 80 are particularly useful. The addition of at least one surfactant, particularly a non-ionic as described above, to the liquid compositions of the present invention, improves the dispersion properties of diclofenac potassium relative to compositions not containing such non-ionic surfactant. This in turn provides a more rapid onset of the therapeutic benefits provided by diclofenac potassium with reduced gastroirritation in a mammal relative to compositions not containing the surfactant.

As used in the present invention, the concentration of the sum of non-ionic surfactant utilized, wherein more than one such surfactant can be utilized, generally ranges from about zero percent to about 10 percent (w/w), with a range from about 1 percent to about 5 percent (w/w) being preferred. A particularly useful concentration is about 3 percent (w/w).

Typically, the order of addition of the various components comprising the present invention will not affect the formation of a solution, when desired, of the present invention. However, when such a surfactant is used, it may be best to add the surfactant or surfactants following addition of diclofenac active ingredient and dispersing agent.

It should be understood that each component comprising the compositions of the present invention must be pharmaceutically acceptable and utilized in a non-toxic concentration. Other pharmaceutically acceptable, non-toxic pharmaceutical additives may be included in the compositions of the present invention and include, for example, sweetening agents, local anesthetics, antibacterials, a lower alkyl alcohol such as ethanol, and the like.

Commonly used pharmaceutical agents, such as, for example, about 0.1 N to 6 N hydrochloric acid, are used in the liquid formulation as a stabilizing agent for softgel capsule. A preferred pH range of the present compositions when used for filling soft gelatin capsules is from about 4.0 to about 9.0.

The resulting oral administrable composition comprising diclofenac potassium in a dispersible liquid formulation exhibits improved dispersing properties of the diclofenac potassium upon contact with stomach acid, which results in faster, reproducible, and a more uniform absorption rate than conventional pharmaceutical compositions. A more rapid, uniform absorption of the diclofenac potassium generally provides a more rapid onset of the therapeutic benefits.

The oral dispersible liquid formulations of the present invention are usually formulated to deliver a dosage level of between about 13 to about 30 mg, usually between about 14 mg to about 25 mg, of diclofenac potassium for total dosage amount of up to about 100 mg per day. This formulation may also be used to fill capsules such as hard or soft gelatin capsules. The preparation of such capsules is well known in the pharmaceutical art [see, e.g. Modem Pharmaceutics, Third Edition, (G. S. Banker and C. T. Rhodes, ed.; 1996); and The Theory and Practice of Industrial Pharmacy, Third Edition, (L. Lachman, H. A. Lieberman, and J. L. Kanig, ed.; 1986)].

Pain Management After Bunionectomy:

A bunion or hallux valgus is an inflammation or thickening of the joint capsule of the great toe. This inflammation causes injury and deformity to the joint due to abnormal bone growth. The great toe is forced in toward the rest of the toes, causing the head of the first metatarsal bone to jut out and rub against the side of the shoe; the underlying tissue becomes inflamed and a painful growth forms. As this bony growth develops, the bunion is formed as the big toe is forced to grow at an increasing angle towards the rest of the toes. A bunion may also develop in the fifth metatarsal bone, in which case it is known as a bunionette or tailor's bunion. Bunions often develop from wearing narrow, high-heeled shoes with pointed toes, which puts enormous pressure on the front of the foot and causes the foot and toes to rest at unnatural angles. Injury in the joint may also cause a bunion to develop over time. Genetics play a factor in 10% to 15% of all bunion problems; one inherited deformity, hallux valgus, causes the bone and joint of the big toe to shift and grow inward, so that the second toe crosses over it. Flat feet, gout, and arthritis increase the risk for bunions.

Bunion surgery, usually called a bunionectomy, is almost always done as an outpatient procedure. The procedure itself varies depending on the type and severity of the deformity. Although the procedure varies, the recovery is the same for all. Some of the bunionectomy procedures are named Akin, Austin Akin, Keller, Silver, Silver Akin, and Kalish depending on which area of the bone is cut and the type of cut that is made. Once the subject is in the operating room and after anesthesia has been started, a tourniquet is applied to either the thigh or ankle depending on the type of anesthesia. The tourniquet is used to prevent bleeding during surgery. After the tourniquet is applied, the foot and lower leg are washed in a sterile fashion to help prevent infection. The surgeon then makes an incision at the top of the great toe into the joint capsule.

Once the bone is exposed, the surgeon makes a cut in the bone in order to correct the deformity. This is called an "osteotomy". As defined herein, an osteotomy is a surgical procedure in which a bone is cut to shorten, lengthen or change its alignment. It is used for example to straighten a bone that has healed crookedly following a fracture. Bone is defined herein as a connective tissue consisting of bone-building osteoblasts, stationary osteocytes, and bone-destroying osteoclasts, embedded in a mineralized matrix infused with spaces and canals. In the case of the hallux valgus, a small piece of bone is removed and the bone realigned to correct the deformity. Tendon and other soft tissue correction may also be required in order to assure full correction is made.

Depending on the type of bunionectomy, fixation may be required. Fixation may be internal, percutaneous or by external means such as a cast or splint, surgical shoe, adhesive form or a dressing. In the bunionectomy the fixation is often internal. This is usually done with either screws or wire. Once the bone is realigned, the wound is irrigated with warm sterile saline and then sutured closed and a dressing applied. Recovery varies according to extent of the surgical procedure and each individual's rate of healing.

Usual post-operative care consists of rest, elevation, and ice for the first 3-5 days. Depending on the procedure performed some walking may be done in a special shoe during this time. A check-up is performed in the office and the bandage is changed. Often subjects will return to work after 3-7 days, depending on the requirements of the job. Skin usually heals in two weeks and at this time the stitches are removed. Bone takes 6-8 weeks to heal. Taking X-rays at regular intervals can assess the rate of bone healing. Any bunion surgery results in some stiffness. Physical therapy starts at the second or third week to minimize this stiffness, usually home exercises are sufficient. If these exercises are not performed, a poor result may occur due to excessive stiffness. Swelling gradually decreases and, at two months, providing sufficient healing of the bone has occurred, regular shoes may be worn. Regular activities can often be resumed at two to three months as tolerated. Some swelling may be present for six months or more. The recovery period varies according to procedure and each individual's rate of healing. Some factors such as circulation, smoking, bone quality, and general health can also have an effect.

Treatment for pain after bunionectomy surgery typically consists of opioid and/or NSAIDs/COX-2 inhibitors. In some cases, opioid are given for the first 3-5 days and then the subject is treated with an NSAID or COX-2 Inhibitor. However, interest in the cardiovascular risk associated with the use of NSAID/COX-2 inhibitors has become intense, raising serious questions regarding the use of such agents. It has been discovered that an oral administrable composition comprising low dosages (e.g. between about 13 mg to about 30 mg) of diclofenac potassium, in a dispersible liquid formulation (relative to conventional dosage amounts of 50 mg or more) is surprisingly effective in providing immediate effective relief of moderate to severe acute pain to patients following post-surgical procedures, particularly outpatient post-surgical procedures such as bunionectomy, such that the need for opioids can be delayed, reduced or eliminated altogether. Furthermore, the reduction of the unit dosage amount of diclofenac potassium can lead to a substantial reduction or elimination of the risk of a cardiovascular event.

The term "acute pain" as used herein means pain that has a sudden onset and commonly declines over a short time (days hours, minutes) and follows injury to the body and which generally disappears when the bodily injury heals. The intensity of the acute pain following a bunionectomy can be mild to moderate, moderate to moderately severe, or moderate to severe.

Pain rating scales are used in daily clinical practice to measure pain intensity. The commonly used measurement scales include the Visual Analog Scale (VAS), the Graphic Rating Scale (GRS), the Simple Descriptor Scale (SDS), the Numerical Rating Scale (NRS), and the Faces Rating Scale (FRS). All of these scales have been documented as being valid measures of pain intensity. The three scales most commonly used in the U.S. are the numerical, word and faces scales.

The visual analog scale (VAS) is a 10 cm. vertical or horizontal line with word anchors at the extremes, such as "no pain" on one end and "pain as bad as it could be" at the other. The patient is asked to make a mark along the line to represent pain intensity.

The graphic rating scale (GRS) is a variation of the visual scale which adds words or numbers between the extremes. Wording added might include "no pain", "mild", "severe".

The descriptor scale (SDS) is a list of adjectives describing different levels of pain intensity. For example pain intensity may be described as "no pain", "mild", "moderate" or "severe".

The numerical pain rating scale (NPRS) refers to a numerical rating of 0 to 10 or 0 to 5 or to a visual scale with both words and numbers. The patient is asked to rate the pain with 0 being no pain and 10 being the worst possible pain. The faces scale was developed for use with children. This scale exists in several variations but relies on a series of facial expressions to convey pain intensity.

Grouping patients' rating of pain intensity as measured with a numerical scale ranging from 0 to 10 into categories of mild, moderate, and severe pain is useful for informing treatment decisions, and interpreting study outcomes,. In 1995, Serlin and colleagues (Pain, 1995, 277-84) developed a technique to establish the cut points for mild, moderate, and severe pain by grading pain intensity and functional inference. Since then, a number of studies have been conducted to correlate the numerical scales, for example the NPRS, with cutpoints related to levels of pain intensity. Common severity cutpoints are (1 to 4) for mild pain, (5 to 6) for moderate pain, and (7 to 10) for severe pain.

The term "patient" as used herein refers to a warm blooded animal such as a mammal which is the subject of surgical trauma. It is understood that at least dogs, cats, mice and humans are within the scope of the meaning of the term.

As used herein, the term "treatment", or a derivative thereof, contemplates partial or complete inhibition of acute pain, when a composition of the present invention is administered following the onset of acute pain.

In one embodiment, a method is provided for treatment of acute pain following a post-surgical procedure, particularly following an osteotomy such as a bunionectomy. The method comprising orally administering to the patient between about 13 to about 30 mg, usually about 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 22.5 mg, 25 mg, 27.5 mg, 28 mg or 30 mg of diclofenac potassium in a dispersible liquid formulation. Suitable oral dispersible liquid formulations are described, for instance, in U.S. Pat. Nos. 5,183,829 and 6,365,180, which is incorporated by reference in its entirety.

The diclofenac potassium in the dispersible liquid formulation can be administered about every 4 hours to 8 hours for a period of at least about 24 hours, at least about 36 hours, at least about 48 hours, at least about 72 hours, at least about 96 hours, at least about 120 hours, or at least about 144 hours or at least about seven (7) days, wherein the daily total amount of diclofenac potassium administered is less than or equal to about 100 mg.

In a specific embodiment, a dosage amount of about 25 mg diclofenac potassium in a dispersible liquid formulation has been found to be suitable for treating acute pain, e.g., mild to moderate, moderate to moderately severe, or moderate to severe, resulting from post-surgical trauma, e.g., such as that resulting from an osteotomy. A dosage amount of 25 mg diclofenac has been found to be particularly effectively for treating post-bunionectomy acute pain.

In a specific embodiment, diclofenac potassium salt in a dispersible liquid formulation in the dosage amounts discussed above can be administered at an interval of at least about 4 hours, at least about 5 hours, at least about 6 hours, or at least about 8 hours. The administered amount of diclofenac potassium salt can be effective in providing acute pain relief for about 4 to about 8 hours, preferentially for about 6 to about 8 hours, after administration.

In a specific embodiment, the method of the invention utilizes about 25 mg of diclofenac potassium contained in a dispersible liquid formulation contained in a liquid-filled, soft gelatin capsule. The formulation includes a combination of polyethylene glycol 400, glycerin, sorbitol, povidone, polysorbate 80, and hydrochloric acid, isopropyl alcohol, and mineral oil.

In a specific embodiment, the diclofenac potassium composition useful in the inventive method can provide a plasma concentration of diclofenac in a patient ranges between about 670 to about 1500 ng/ml in less than 30 minutes with the concomitant onset of relief of acute pain.

In a specific embodiment, the administration of diclofenac potassium composition in accordance with the inventive method can result in immediate increase in plasma concentration of diclofenac characterized by T(max) of about 0.47.

In a specific embodiment, the diclofenac potassium composition useful in the method of the invention provides the following mean pharmacokinetic characteristics of: a terminal half-life (hr) of 1.07+0.29; a Cmax (ng/mL) of 1087+419; and an AUC (0 to infinity) (ng.h/mL) of 597+151.

In another embodiment, diclofenac is substantially eliminated from plasma in the first 2 hours following administration. As defined herein, the phrase "substantially eliminated" means at least about 75%, 80%, 85%, 90% or 95% of diclofenac is eliminated from plasma in the first 2 hours or after about the first 2 to 3 hours.

The following examples provide a representative composition comprising diclofenac potassium in a dispersible liquid formulation (Example 1) and method of treating post-bunionectomy acute pain using diclofenac potassium in a dispersible liquid formulation (Example 2). The materials, methods, and examples herein are illustrative only and, except as specifically stated, are not intended to be limiting.

EXAMPLES

Example 1

Preparation of Liquid Diclofenac Potassium Formulation

A typical formulation used in pain treatment is summarized in Table 1:

TABLE 1

| Ingredient | Description | A % w/w | B % w/w | C % w/w |
|---|---|---|---|---|
| Diclofenac Potassium (25 mg) | Active | 6.25 | 6.25 | 6.25 |
| PEG 400 NF | Dispersing agent; Solubilizing agent | 70.12 | 69.70 | 66.95 |

TABLE 1-continued

| Ingredient | Description | A % w/w | B % w/w | C % w/w |
|---|---|---|---|---|
| Glycerin | Co-solvent; Plasticizing agent | 10.0 | 10.0 | 10.0 |
| Sorbitol Solution 70% | Solubilizing agent; Stabilizing agent; Plasticizing agent | 5.0 | 5.0 | 5.0 |
| Povidone USP (PVP K-30) | Dispersing agent; | 6.3 | 6.3 | 6.3 |
| Polysorbate 80 | Emulsifying agent; Surfactant | 1.5 | 1.5 | 3.0 |
| 6N HCl | Softgel Stabilizing agent | 0.83[2] | 1.25 | NA |
| 2N HCl | Softgel Stabilizing agent | NA | NA | 2.5 |
| Nitrogen Gas (if stored prior to filling) | | Overlay | Overlay | Overlay |

PEG 400 was heated to about 45° C. in a cowls mixer. One half of Polysorbate 80 was then added to the heated PEG 400 and mixed while maintaining the temperature at about 45° C. Diclofenac potassium was then added and mixed to dissolve while maintaining the temperature, followed by addition of Povidone to the mixture. The contents were mixed to dissolve new additions at each step while maintaining the temperature at 45° C. The mixture was cooled to about 25-30° C. while continuing to mix. 6N HCL subsequently added and mixed followed by mixing remaining Polysorbate 80 into the mixture. Glycerin and Sorbitol were then added and mixed while continuing to maintain the temperature at about 25-30° C. The final pH to about 6. The solution was filtered and filled into 25 mg soft gelatin capsules (400 mg fill weight).

Example 2

Method for Treatment of Post-Surgical Acute Pain Using Liquid Diclofenac Potassium Formulation Clinical studies were conducted to determine the analgesic efficacy of Diclofenac Potassium Soft Gelatin Capsules (DPSGC) 25 mg in acute surgical pain. The study was a placebo controlled study in subjects recovering from bunionectomy surgery. A total of 201 subjects, 102 in the DPSCG group and 99 in the placebo group, were enrolled, randomized and received at least one dose of study drug. Three subjects, 1 in the DPSCG and 2 in the placebo group discontinued.

The primary efficacy variable was the average pain intensity over a 48-hour multiple dose period calculated using an 11-point Numerical Pain Rating Scale (NPRS).

Other variables analyzed to evaluate analgesic effect of Diclofenac Potassium Soft Gelatin Capsules included:
(1) Evaluation of the analgesic efficacy of a single dose of DPSGC (during the initial dosing period) with individual pain intensity assessments as compared to placebo;
(2) Evaluation of the time needed to re-medication (during the initial dosing period) of a single dose of DPSGC as compared to placebo;
(3) Evaluation evaluate the frequency and timing (defined as time of meaningful pain relief) of obtaining clinically significant analgesic efficacy (defined as a 30% reduction in pain intensity) as compared to placebo in acute pain;
(4) Evaluation of the use of rescue medication during the multiple dose period;
(5) Evaluation of the time to onset of obtaining a ≧30% reduction in pain intensity, as compared to placebo, and its duration in acute pain; and
(6) Evaluation of the safety and tolerability of DPSGC 25 mg when used for the treatment of acute surgical pain.

The efficacy measures in the study included the NPRS, the Pain Relief Rating Scale, and the Time to Meaningful, Perceptible Pain Relief, and a Global Assessment of Study Medication.

Numerical Pain Rating Intensity Scale (NPRS):

The 11-point NPRS was utilized to assess the primary endpoint. At each time point, subjects evaluated their current pain intensity relative to an 11-point numerical rating scale. A score of zero represented no pain and a score of 10 represented worst possible pain.

Subjects were instructed to: "Rate your pain by recording the one number that best describes the amount of pain you have at this time."

| 0 | 1 | 2 | 3 | 4 | 5 | 6 | 7 | 8 | 9 | 10 |
|---|---|---|---|---|---|---|---|---|---|---|
| No Pain | | | | | | | | | | Worst Possible Pain |

Pain Relief Rating Scale:

Subjects assessed their level of pain relief using a 5-point Pain Relief Rating Scale. A worksheet with a list of adjectives was provided to the subject, and the subject was asked to respond to the following question: "How much relief do you have from your starting pain?"

| | |
|---|---|
| 0 | No pain relief |
| 1 | A little pain relief |
| 2 | Some pain relief |
| 3 | A lot of pain relief |
| 4 | Complete pain relief |

Time to Meaningful and Perceptible Pain Relief:

When the subject received study medication, the Study Coordinator started 2 stopwatches and covered the time displays. To determine the exact moment that the subject began to obtain first perceptible relief, the subject was given the stopwatch 3-4 minutes after dosing and was instructed as follows: "Stop the stopwatch when you have perceptible pain relief, that is, when the relief from pain is first noticeable to you."

Determination of the exact moment that the subject began to obtain meaningful relief was attained similarly, except that the question was: "Stop the stopwatch when you have meaningful pain relief, that is, when the relief from pain is meaningful to you."

The elapsed time for each of these determinations was recorded.

Subject Global Assessment of Study Medication:

The subject provided an overall (global) evaluation of the study medication on a 5-point categorical scale. A worksheet with ratings was given to the subject, and the subject was asked to respond to the following question: "How would you rate this study medication as a pain reliever?"

1 Poor
2 Fair
3 Good
4 Very good
5 Excellent

Secondary Efficacy Endpoints

Secondary efficacy endpoints were onset of perceptible and meaningful pain relief during the single-dose period on Day 1, TOTPAR during the single-dose period on Day 1, and onset of 30% reduction from baseline in pain intensity during the single-dose period on Day 1. further descriptionsof these endpoints follow.

Onset of perceptible and meaningful pain relief was based on double stopwatch method and measured on Day 1. Subjects who discontinued the study before onset were censored at the time of the last on-study NPRS evaluation. Subjects who received rescue medication or study drug re-medication before onset were censored at the time that rescue medication or study drug was administered. Total Pain Relief (TOTPAR) was calculated with the trapezoidal rule for the pain relief at 10, 15, 20, 30, 45, and 60 minutes and at 1.5, 2, 2.5, 3, 4, 5, 6, 7, and 8 hours after the initial dose on Day 1 or until the time of re-medication. The calculation was similar to that for the SPID (described below). Imputation of missing values before re-medication was performed with the WOCF (worst observation carried forward) approach as defined for the primary efficacy endpoint.

The onset of a ≧30% reduction in pain intensity after the administration of the first dose of the study drug on Day 1 was measured. Subjects who discontinued the study before onset were censored at the time of the last on-study NPRS evaluation. Subjects who received rescue medication or study drug re-medication before onset were censored at the time that rescue medication or study drug was administered.

The sum of Pain Intensity Differences (SPID) over the 48-hour multiple dose period was measured. Differences were calculated from the pre-Dose 1 pain assessment on Day 1. Imputation of missing scheduled observations and of pain assessments following rescue medication was performed with the same method used for the primary efficacy endpoint. Pain assessments at the time of rescue medication and scheduled pain assessments (imputed or observed) were included in the calculation. The calculation method for the Day 1 SPID (described below) was used.

Sum of Pain Intensity Differences (SPID) was calculated with the trapezoidal rule for the pain intensity differences at 10, 15, 20, 30, 45, and 60 minutes and at 1.5, 2, 2.5, 3, 4, 5, 6, 7, and 8 hours after the initial dose on Day 1 or until the time of re-medication. The area between 2 consecutive time points was calculated as ([time 2–time 1]×[pain intensity difference at time 2+pain intensity difference at time 1])/2. Imputation of missing values before re-medication was performed with the WOCF approach as defined for the primary efficacy endpoint.

Pain intensity, pain intensity difference, and pain relief were measured at 10, 15, 20, 30, 45, and 60 minutes and at 1.5, 2, 2.5, 3, 4, 5, 6, 7, and 8 hours after the initial dose on Day 1 or until the time of re-medication. Pain intensity was assessed using the NPRS and the pain intensity difference was calculated as the change in pain intensity from baseline to the time point. Pain intensity at pre-Dose 1 was considered baseline. Pain relief was assessed using a 5-point relief rating scale (0=no relief, 4=complete pain relief). Imputation of missing values before re-medication was performed with the WOCF approach as defined for the primary efficacy endpoint.

Proportion of subjects requiring rescue medication, total number of rescues on each postoperative day, and quantity of rescue medication on each postoperative day was measured. Postoperative day was the same as calendar day. If no rescue medication was required for a subject, the total number of rescues and quantity of rescue medication were counted as zero. Otherwise, missing data were not imputed.

Mean rescue interval during the multiple dose period (Days 1-4) was measured. The mean rescue interval was calculated from the rescue intervals during each 6-hour dosing interval for postoperative Days 1-4. The rescue interval was defined as the difference between the dosing time and either the time that a rescue medication was taken (if any) or the time of the next study drug administration, whichever was less.

Proportion of subjects discontinuing due to inadequate pain relief, was recorded on the Day 5 completion CRF(case report form). This included subjects who discontinued due to inadequate pain relief during the single-dose portion of the study.

Subjects' global assessment of study drug at discharge and on Day 5 or early termination was measured.

Time to re-medication following the initial dose on Day 1 was measured. Subjects who discontinued the study before study drug re-medication were censored at the time of the last on-study NPRS evaluation. Subjects who received rescue medication before study drug re-medication were censored at the time that rescue medication was administered.

The duration of obtaining a >30% reduction in pain intensity after the administration of the first dose of the study drug on Day 1 was measured.

Proportion of subjects achieving clinically significant analgesic efficacy after the administration of the first dose of the study drug on Day 1 was monitored. Clinically significant analgesic efficacy was defined as both ≧30% reduction from baseline pain intensity using NPRS and meaningful relief as indicated by the stopwatch method. The events may have occurred at any time after dosing on Day 1 and the 2 events may have occurred at different times on Day 1. Subjects were considered failures for this endpoint if they discontinued the study or received study drug re-medication before the last event occurred.

Proportion of subjects experiencing mild to no pain (NPRS≦2) after the administration of the first dose of study drug on Day 1. Subjects were considered failures for this endpoint if they discontinued the study, received rescue medication, or received study drug re-medication before experiencing mild to no pain.

SPID and TOTPAR were analyzed with an analysis of covariance or ANCOVA model having factors for treatment and site and with the baseline value (pain intensity NPRS Score) as covariate. The 2-way ANOVA with factors for treatment and site was used to analyze average rescue interval and duration of a ≧30% reduction in pain intensity. The number of rescues on each day and the amount of rescue medication on each day were analyzed for treatment differences with the Wilcoxon test.

The treatment-by-site interaction was assessed in a supportive ANCOVA model for the primary endpoint. If the treatment-by-site interaction was statistically significant, exploratory data analysis could have been performed to provide an adequate description of the interaction. If a quantitative interaction was present, the overall treatment effect was to be estimated over sites based on the final model with the interaction effect and all other statistically significant effects. If a qualitative interaction was present, the potential cause of the interaction (such as subject characteristics, clinic management, data/CRF handling) was to be explored.

Least squares means (LS-means) for each treatment, differences in the LS-means between the treatments, and 95% confidence intervals for the treatment difference in LS-means were also provided for endpoints analyzed with the 2-way analysis of variance, ANOVA, or analysis of covariance, ANCOVA.

Categorical efficacy endpoints were analyzed with the Cochran-Mantel-Haenszel test with site as the stratification factor. Endpoints included the proportion of subjects achieving clinically significant analgesic efficacy, proportion of subjects requiring rescue medication, proportion of subjects discontinuing due to inadequate pain relief, global assessment of study drug, proportion of subjects achieving no or mild pain, pain intensity at each time point, pain intensity difference at each time point, and pain relief at each time point.

All time-to-event efficacy endpoints were summarized for each treatment group using Kaplan-Meier survival curves. This method estimated the median and 95% confidence limits for the time-to-event in each treatment group. Treatment groups were compared using a log-rank test. In addition, a Cox proportional hazard model was used with effects for treatment, baseline pain intensity score (based on the Pain Intensity NPRS score), and any demographic characteristic that was found to be statistically significantly different between treatment groups (if any) ($p \leq 0.05$). The treatment factor was parameterized using reference cell parameterization with placebo as the reference group such that the parameter estimate for the DPSGC 25 mg product represented the adjusted treatment effect and the Wald Chi-Square statistic provided a test of the DPSGC 25 mg product vs. placebo effect.

Treatment Regimen:

This was a multicenter, randomized, double-blind, parallel-group, placebo-controlled study in subjects recovering from bunionectomy surgery. The study consisted of 2 dosing periods: an initial dosing period (on Day 1) followed by a multiple dose period (through Day 4).

Subjects were provided 1-2 tablets of hydrocodone/acetaminophen (APAP) (5 mg/500 mg) every 4 to 6 hours as needed for pain, not to exceed 8 tablets daily during the day of surgery and up until 4 hours before the treatment study began. Analgesic use was recorded. If subjects required pain medication other than that specified per protocol, they were discontinued. The use of ice packs was allowed on Day 0 and on Day 1 up to 3 hours after the last analgesic dose taken prior to randomization (study medication dose 1) but not after randomization during Days 1-4.

Upon awakening at 4 am or later on the morning of Day 1 (initial dosing period), subjects who complained of having increased pain assessed their pain intensity at rest (no activity of the affected toe for at least 10 minutes prior to pain assessments) using the 11-point NPRS (0=no pain, 10=worst pain imaginable). When subjects first reported a pain intensity score of at least 4 between 4 am and 10 am, they were randomly allocated to 1 of 2 blinded treatment arms: Arm A (placebo) or Arm B (25 mg DPSGC). All pain medication (i.e., hydrocodone/APAP) was to have been discontinued at least 4 hours before the initial dose of study medication.

After taking the first dose, subjects were provided 2 stopwatches to record the time to onset of perceptible pain relief and the time to onset of meaningful pain relief. Pain intensity and pain relief assessments and vital signs were measured at various time points after the initial dose or until the time of re-medication.

The second dose (re-medication) was given to the subject when the subject requested the second dose to treat his/her pain. If the subject did not indicate a need for re-medication within 8 hours of taking the first dose of study medication, he/she was given the second dose of study medication at 8 hours.

The re-medication dose was the second dose of the study and marked the start of the 48-hour assessment period, during which subjects took their study medication every 6 hours. Following the re-medication dose, subsequent doses while in the study unit occurred every 6 hours (+/−1 hour from the 6-hour schedule established at the time of re-medication). Study medication use was not to exceed 4 doses in one 24-hour period. Subjects were discharged after the 48-hour period was completed and were instructed to take their medication on an outpatient basis at 6 am, 12 pm, 6 pm and 12 am. The last dose of study medication was taken at 12 midnight on Day 4.

Rescue medication consisting of hydrocodone/APAP (5 mg/500 mg) was available for the subjects after the re-medication dose. However, subjects were encouraged to delay taking rescue medication until at least 1 hour after receiving study medication. Subjects who took rescue medication recorded a pain assessment at the time of rescue and took the subsequent doses of study medication on schedule. They continued the remaining pain assessments.

The primary efficacy endpoint of the average of pain intensity over 48 hours was analyzed using an analysis of covariance (ANCOVA) model with factors for treatment and site and baseline pain intensity score (using the pain intensity NPRS Score; 0=no pain, 10=worst pain imaginable) as a covariate.

SPID and TOTPAR were analyzed with an ANCOVA model having factors for treatment and site and with the baseline value (pain intensity NPRS Score) as covariate. The 2-way analysis of variance (ANOVA) with factors for treatment and site was used to analyze average rescue interval and duration of a $\geq 30\%$ reduction from baseline in pain intensity. The number of rescues on each day and the amount of rescue medication on each day were analyzed for treatment differences with the Wilcoxon test. The treatment-by-site interaction was assessed in a supportive ANCOVA model for the primary endpoint. Least squares means (LS-means) for each treatment, differences in the LS-means between the treatments, and 95% confidence intervals for the treatment difference in LS-means were also provided for endpoints analyzed with the 2-way ANOVA or ANCOVA.

Categorical efficacy endpoints were analyzed with the Cochran-Mantel-Haenszel test with site as the stratification factor. All time-to-event efficacy endpoints were summarized for each treatment group using Kaplan-Meier survival curves. In addition, a Cox proportional hazard model was used with effects for treatment and baseline pain intensity score (based on the Pain Intensity NPRS Score). Pain measures taken after re-medication or use of rescue medication were considered missing and replaced using worst observation carried forward (WOCF) methodology.

Evaluation of Efficacy of Analgesic Effect of Liquid Formulation of Diclofenac Potassium:

The primary efficacy assessment endpoint was the average pain intensity over the 48-hour multiple dose period. Pain intensity was measured using a NPRS of 0 to 10 (0=no pain, 10=worst possible pain).

All observed, scheduled NPRS pain assessments were averaged for each subject over the 48-hour multiple dose period, unless rescue medication was administered. If rescue medication was administered, scheduled pain assessments were considered missing for 6 hours following administration of rescue medication and the pain assessment at the time of rescue medication was carried forward. If rescue medication was administered more than once within 6 hours, the pain assessment at the first rescue was carried forward until there had been at least 6 hours since the use of last rescue. Pain assessments at the time of rescue medication and scheduled pain assessments (imputed or observed) were included in the average pain intensity over the 48-hour multiple dose period. Missing scheduled pain assessments for subjects who did not prematurely discontinue from the study were imputed with the worst observation carried forward (whether it was the baseline or some other value) up to the time of the missing observation (regardless of whether the worst value occurred in association with rescue medication). For subjects who prematurely discontinued from the study, the worst observation (whether it was the baseline or some other value) was carried forward for the remainder of the 48-hour multiple dose period (regardless of whether the worst value occurred in association with rescue medication).

The primary efficacy endpoint of the average of pain intensity over 48 hours was analyzed using an ANCOVA model with factors for treatment and site and baseline pain intensity score (using the pain intensity NPRS Score) as a covariate. The baseline pain intensity score was the last pain intensity score obtained before study drug dosing on Day 1.

The 3-hour post-dose pain assessment was not required if it fell between midnight and 5 am. If these values were not obtained, they were not considered missing data points and were not imputed.

Subjects recorded their pain intensity post-operatively on a 0-10 numerical pain rating scale (NPRS). A clinically significant difference was felt to be 1.5 units on the NPRS for the average pain intensity over 48 hours with the NPRS. If the common standard deviation was 3.0, then a sample size of 86 subjects per group would provide over 90% power to detect as significant a difference of 1.5 units between the placebo and active groups using a two-sample t-test with a significance level of 0.05 two-sided.

No statistically significant difference was observed between the DPSGC 25 mg and placebo groups for the mean NPRS pain intensity score at baseline (6.89 and 7.29, respectively). The difference between the treatment groups in average pain intensity over the 48-hour multiple dose period, calculated using the 11-point NPRS, was statistically significant in the full analysis population (Table 2).

TABLE 2

| Primary Endpoint | Placebo | DPSGC 25 mg | p-value |
| --- | --- | --- | --- |
| Average 48-Hour Pain Intensity NPRS Score | 5.56 | 2.49 | <0.0001 |

In the full analysis population, the difference between the treatment groups in average pain intensity over the 48-hour multiple dose period, calculated using the 11-point NPRS was statistically significant using the WOCF methodology (p<0.0001). A lower average pain score was observed in the DPSGC 25 mg group compared to the placebo group (2.49 vs. 5.56). This substantial difference (greater than 2 points) in average pain intensity would be expected to provide a significant clinical benefit to subjects. Results were similar in the evaluable population and when LOCF (last observation carried forward) and observed cases methodologies were used. A summary of average pain intensity over the 48-hour multiple dose period for the full analysis and evaluable populations is presented in Table 3.

TABLE 3

Average 48-Hour Pain Intensity NPRS Score During Multiple Dose Period (Full Analysis and Evaluable Populations)

| Population (Imputation Method) | Placebo | DPSGC 25 mg | p-value[a] |
| --- | --- | --- | --- |
| Full Analysis (WOCF) | (N = 99) | (N = 102) | <0.0001 |
| Mean (SD) | 5.56 (2.026) | 2.49 (1.967) | |
| Median | 5.65 | 1.85 | |
| Min-Max | 0.50-10.00 | 0.00-7.83 | |
| LS-mean | 5.60 | 2.71 | |
| Difference in LS-means | 2.89 | | |
| 95% CI for difference in LS-means | 2.43, 3.35 | | |
| Evaluable (WOCF) | (N = 95) | (N = 96) | <0.0001 |
| Mean (SD) | 5.44 (1.950) | 2.39 (1.926) | |
| Median | 5.53 | 1.76 | |
| Min-Max | 0.50-9.58 | 0.00-7.83 | |
| LS-mean | 5.50 | 2.56 | |
| Difference in LS-means | 2.94 | | |
| 95% CI for difference in LS-means | 2.48, 3.39 | | |

WOCF = worst observation carried forward;
SD = standard deviation;
Min = minimum;
Max = maximum;
LS-mean = least squares means
[a]From ANCOVA with factors for treatment and site, and with baseline pain intensity as covariate.

No statistically significant interactions of treatment with study site and baseline pain severity were observed. All of the factors were statistically significant in the model.

Results for the secondary endpoints in the full analysis population for both the 48-hour multiple dose and 8-hour initial dosing periods are summarized in Table 4.

TABLE 4

| Secondary Endpoints in Inpatient 48-Hour Multiple Dose Period | Placebo | DPSGC 25 mg | p-value |
| --- | --- | --- | --- |
| Mean SPID | 90.26 | 210.01 | <0.0001 |
| Mean peak PID | 5.47 | 6.44 | <0.0001 |
| Mean rescue interval (minutes) | 263.88 | 331.54 | <0.0001 |
| Rescue use | | | |
| Proportion of subjects on Day 1 | 87.9% | 39.2% | <0.0001 |
| Proportion of subjects on Day 2 | 64.6% | 21.6% | <0.0001 |
| Proportion of subjects on Day 3 (up to discharge) | 29.3% | 4.9% | <0.0001 |
| Subject's global assessment at discharge | n (%) | n (%) | |
| Poor | 25 (25.3%) | 1 (1.0%) | |
| Fair | 15 (15.2%) | 6 (5.9%) | |
| Good | 24 (24.2%) | 14 (13.7%) | |
| Very Good | 19 (19.2%) | 28 (27.5%) | |
| Excellent | 15 (15.2%) | 52 (51.0%) | |
| Mean response | 2.84 | 4.23 | <0.0001 |

TABLE 5

| Secondary Endpoints in Inpatient 8-Hour Initial Dosing Period | Placebo | DPSGC 25 mg | p-value |
| --- | --- | --- | --- |
| Mean SPID | 4.06 | 11.67 | <0.0001 |
| Peak pain relief | 1.44 | 2.19 | 0.0006 |
| Mean TOTPAR | 2.63 | 8.16 | <0.0001 |
| Proportion of subjects achieving perceptible pain relief | 69.7% | 82.4% | 0.0380 |

TABLE 5-continued

| Secondary Endpoints in Inpatient 8-Hour Initial Dosing Period | Placebo | DPSGC 25 mg | p-value |
|---|---|---|---|
| Median onset to perceptible pain relief (minutes) | 22.18 | 26.01 | 0.2348 |
| Proportion of subjects achieving meaningful pain relief | 35.4% | 56.9% | 0.0025 |
| Median onset to meaningful pain relief (minutes) | 106.30 | 70.22 | 0.0080 |
| Median time to re-medication (minutes) | 80.00 | 156.50 | <0.0001 |
| Proportion of subjects achieving ≧30% reduction in pain | 40.4% | 60.8% | 0.0043 |
| Median time to onset of ≧30% reduction in pain (minutes) | 150 | 60 | 0.0376 |
| Mean duration of ≧30% reduction in pain (minutes) | 134.08 | 241.44 | 0.0132 |
| Proportion of subjects achieving clinically significant analgesic efficacy after first dose | 29.3% | 52.9% | 0.0008 |
| Proportion of subjects experiencing mild to no pain after first dose | 23.2% | 44.1% | 0.0019 |

Estimated using Kaplan-Meier product limit estimates.

Mean Rescue Interval

Mean interval between protocol-scheduled study drug dosing and administration of rescue medication or the next protocol-scheduled study drug dose (whichever occurred first) during the 48-hour multiple dose period was statistically significantly (p<0.0001) longer in the DPSGC 25 mg group compared to the placebo group, 331.54 vs. 263.88 minutes. Similarly, the mean intervals between dosing and administration of rescue on Day 1, Day 2, and Day 3 (up to discharge) were statistically significantly (p<0.0001) longer in the DPSGC 25 mg group compared to the placebo group The mean interval between dosing and rescue medication lengthened from Day 1 to Day 3 as would be expected, given the natural waning of pain over time after surgery, 308.95 to 350.03 minutes in the DPSGC 25 mg group; 201.55 to 315.66 minutes in the placebo group. The largest increase in the mean interval between dosing and rescue medication occurred between Dose 2 and Dose 3 in both study groups.

Generally, the average time to rescue in the DPSGC 25 mg group was 5.5 to 6 hours, supporting that a 6-hour dosing interval is appropriate. Results were similar in the evaluable population.

A summary of mean interval between dosing and administration of rescue during the 48-hour multiple dose period for the full analysis and evaluable populations is presented in Table 6.

TABLE 6

Overall Mean Interval Between Dosing and Administration of Rescue During the 48-Hour Multiple Dose Period (Full Analysis and Evaluable Populations)

| Overall Mean Rescue Interval (minutes)$_a$ | Placebo | DPSGC 25 mg | p-value$^b$ |
|---|---|---|---|
| Full Analysis Population | (N = 99) | (N = 102) | <0.0001 |

TABLE 6-continued

Overall Mean Interval Between Dosing and Administration of Rescue During the 48-Hour Multiple Dose Period (Full Analysis and Evaluable Populations)

| Overall Mean Rescue Interval (minutes)$_a$ | Placebo | DPSGC 25 mg | p-value$^b$ |
|---|---|---|---|
| Mean (SD) | 263.88 (72.461) | 331.54 (45.181) | |
| Median | 271.88 | 354.19 | |
| Min-Max | 11.0-364.38 | 152.50-365.63 | |
| LS-mean | 258.77 | 325.77 | |
| Difference in LS-means | −67.00 | | |
| 95% CI for difference in LS-means | −82.38, −51.6 | | |
| Evaluable Population | (N = 95) | (N = 96) | <0.0001 |
| Mean (SD) | 269.40 (65.523) | 332.62 (45.351) | |
| Median | 283.75 | 354.38 | |
| Min-Max | 104.38-364.38 | 152.50-365.63 | |
| LS-mean | 263.95 | 327.53 | |
| Difference in LS-means | −63.58 | | |
| 95% CI for difference in LS-means | −78.48, −48.6 | | |

SD = standard deviation;
Min = minimum;
Max = maximum;
LS-mean = least squares mean $_a$Mean rescue interval was defined as the interval between protocol-scheduled study drug dosing and administration of rescue medication or the next protocol-scheduled study drug dose (whichever occurred first). During the inpatient period, a statistically significantly smaller proportion of subjects in the DPSGC 25 mg group compared to the placebo group used rescue medication on Day 1, Day 2, and up to discharge on Day 3.

During the inpatient period, a statistically significantly smaller proportion of subjects in the DPSGC 25 mg group compared to the placebo group used rescue medication on Day 1, Day 2, and up to discharge on Day 3. See Tables 4, 5 and 7 (see Rescue Use).

TABLE 7

Summary of Rescue Medication Use During the 48-Hour Multiple Dose Period (Full Analysis and Evaluable Populations)

| | Placebo | | | DPSGC 25 mg | | |
|---|---|---|---|---|---|---|
| Variable | Day 1 | Day 2 | Day 3 (up to discharge) | Day 1 | Day 2 | Day 3 (up to discharge) |
| Full Analysis Population | | (N = 99) | | | (N = 102) | |
| Rescue Medication Use, n (%) | 87 (87.9%) | 64 (64.6%) | 29 (29.3%) | 40 (39.2%) | 22 (21.6%) | 5 (4.9%) |
| p-value vs. placebo$_a$ | | | | <0.0001 | <0.0001 | <0.0001 |

TABLE 7-continued

Summary of Rescue Medication Use During the 48-Hour Multiple Dose Period (Full Analysis and Evaluable Populations)

| | Placebo | | | DPSGC 25 mg | | |
|---|---|---|---|---|---|---|
| Variable | Day 1 | Day 2 | Day 3 (up to discharge) | Day 1 | Day 2 | Day 3 (up to discharge) |
| Number of Administrations (among users of rescue medications) | | | | | | |
| Mean (SD) | 2.37 (1.221) | 2.17 (1.121) | 1.07 (0.258) | 1.93 (1.047) | 2.09 (1.269) | 1.00 (0.000) |
| Median | 2.00 | 2.00 | 1.00 | 2.00 | 2.00 | 1.00 |
| Min-Max | 1-5 | 1-5 | 1-2 | 1-4 | 1-5 | 1-1 |
| p-value vs. placebo$_b$ | | | | 0.0497 | 0.7782 | 0.5591 |
| Amount of Rescue Medication (Tablets) (among users of rescue medications) | | | | | | |
| Mean (SD) | 3.78 (2.020) | 3.28 (1.804) | 1.62 (0.677) | 3.03 (2.106) | 2.95 (1.889) | 1.40 (0.548) |
| Median | 4.00 | 3.00 | 2.00 | 2.00 | 2.50 | 1.00 |
| Min-Max | 1-8 | 1-10 | 1-4 | 1-8 | 1-8 | 1-2 |
| p-value vs. placebo$_b$ | | | | 0.0553 | 0.4710 | 0.4962 |
| Evaluable Population | | (N = 95) | | | (N = 96) | |
| Rescue Medication Use, n (%) | 83 (87.4%) | 62 (65.3%) | 28 (29.5%) | 36 (37.5%) | 20 (20.8%) | 5 (5.2%) |
| p-value vs. placebo$_a$ | | | | <0.0001 | <0.0001 | <0.0001 |
| Number of Administrations (among users of rescue medications) | | | | | | |
| Mean (SD) | 2.39 (1.218) | 2.18 (1.138) | 1.07 (0.262) | 1.97 (1.055) | 2.10 (1.334) | 1.00 (0.000) |
| Median | 2.00 | 2.00 | 1.00 | 2.00 | 2.00 | 1.00 |
| Min-Max | 1-5 | 1-5 | 1-2 | 1-4 | 1-5 | 1-1 |
| p-value vs. placebo$_b$ | | | | 0.0797 | 0.8005 | 0.5522 |
| Amount of Rescue Medication (Tablets) (among users of rescue medications) | | | | | | |
| Mean (SD) | 3.77 (1.996) | 3.27 (1.830) | 1.61 (0.685) | 3.14 (2.180) | 3.00 (1.974) | 1.40 (0.548) |
| Median | 4.00 | 3.00 | 2.00 | 2.00 | 2.50 | 1.00 |
| Min-Max | 1-8 | 1-10 | 1-4 | 1-8 | 1-8 | 1-2 |
| p-value vs. placebo$_b$ | | | | 0.1255 | 0.5692 | 0.5284 |

SD = standard deviation;
Min = minimum;
Max = maximum
$_a$From Cochran Mantel Haenszel test with site as strata.
$_b$From ANOVA with factors for poolsite and treatment.

Among subjects who used rescue medication, the mean number of rescue medication administrations and mean amount of rescue medication were smaller in the DPSGC 25 mg group compared to the placebo group on Day 1, Day 2, and Day 3 (up to discharge); a statistically significant treatment difference occurred on Day 1 for number of administrations. See Table 7.

Use of and Amount of Rescue Medication after Discharge

After discharge on Day 3 during the outpatient period, a statistically significantly smaller proportion of subjects in the DPSGC 25 mg group compared to the placebo group used rescue medication on Day 3 (12.7% vs. 39.4%; p<0.0001) and on Day 4 (9.8% vs. 38.4%; p<0.0001 in the full analysis population. Results were similar in the evaluable population.

A summary of rescue medication use after discharge on Day 3 during the outpatient period for the full analysis and evaluable populations is presented in Table 8.

TABLE 8

Summary of Rescue Medication Use After Discharge on Day 3 During the Outpatient Period (Full Analysis and Evaluable Populations)

| | Placebo | | | DPSGC 25 mg | | |
|---|---|---|---|---|---|---|
| Variable | Day 3 (after discharge) | Day 4 | Day 5 | Day 3 (after discharge) | Day 4 | Day 5 |
| Full Analysis Population | | (N = 99) | | | (N = 102) | |
| Rescue Medication Use, n (%) | 39 (39.4%) | 38 (38.4%) | 9 (9.1%) | 13 (12.7%) | 10 (9.8%) | 7 (6.9%) |
| p-value vs. placebo$_a$ | | | | <0.0001 | <0.0001 | 0.5502 |

TABLE 8-continued

Summary of Rescue Medication Use After Discharge on Day
3 During the Outpatient Period
(Full Analysis and Evaluable Populations)

|  | Placebo | | | DPSGC 25 mg | | |
|---|---|---|---|---|---|---|
| Variable | Day 3 (after discharge) | Day 4 | Day 5 | Day 3 (after discharge) | Day 4 | Day 5 |
| Number of Administrations (among users of rescue medications) | | | | | | |
| Mean (SD) | 1.46 (0.643) | 1.92 (1.075) | 1.44 (1.014) | 1.62 (0.650) | 2.30 (1.160) | 1.57 (1.134) |
| Median | 1.00 | 2.00 | 1.00 | 2.00 | 2.00 | 1.00 |
| Min-Max | 1-3 | 1-4 | 1-4 | 1-3 | 1-4 | 1-4 |
| p-value vs. placebo$_b$ | | | | 0.4595 | 0.3340 | 0.8167 |
| Amount of Rescue Medication (Tablets) (among users of rescue medications) | | | | | | |
| Mean (SD) | 1.85 (1.182) | 2.39 (1.264) | 1.67 (1.000) | 2.00 (1.000) | 2.30 (1.160) | 1.57 (1.134) |
| Median | 1.00 | 2.00 | 1.00 | 2.00 | 2.00 | 1.00 |
| Min-Max | 1-6 | 1-4 | 1-4 | 1-4 | 1-4 | 1-4 |
| p-value vs. placebo$_b$ | | | | 0.6755 | 0.8313 | 0.8610 |
| Evaluable Population | | (N = 91) | | | (N = 96) | |
| Rescue Medication Use, n (%) | 35 (38.5%) | 36 (39.6%) | 9 (9.9%) | 12 (12.5%) | 9 (9.4%) | 6 (6.3%) |
| p-value vs. placebo$_a$ | | | | <0.0001 | <0.0001 | 0.3856 |
| Number of Administrations (among users of rescue medications) | | | | | | |
| Mean (SD) | 1.46 (0.657) | 1.94 (1.094) | 1.44 (1.014) | 1.67 (0.651) | 2.44 (1.130) | 1.67 (1.211) |
| Median | 1.00 | 2.00 | 1.00 | 2.00 | 2.00 | 1.00 |
| Min-Max | 1-3 | 1-4 | 1-4 | 1-3 | 1-4 | 1-4 |
| p-value vs. placebo$_b$ | | | | 0.3446 | 0.2296 | 0.7061 |
| Amount of Rescue Medication (Tablets) (among users of rescue medications) | | | | | | |
| Mean (SD) | 1.86 (1.216) | 2.44 (1.275) | 1.67 (1.000) | 2.00 (1.044) | 2.44 (1.130) | 1.67 (1.211) |
| Median | 1.00 | 2.00 | 1.00 | 2.00 | 2.00 | 1.00 |
| Min-Max | 1-6 | 1-4 | 1-4 | 1-4 | 1-4 | 1-4 |
| p-value vs. placebo$_b$ | | | | 0.7183 | 1.0000 | 1.0000 |

SD = standard deviation;
Min = minimum;
Max = maximum
$_a$From Cochran Mantel Haenszel test with site as strata.
$_b$From ANOVA with factors for poolsite and treatment.

Sum of Pain Intensity Difference

Sum of Pain Intensity Difference (SPID) was calculated with the trapezoidal rule for the pain intensity differences at 10, 15, 20, 30, 45, and 60 minutes and at 1.5, 2, 2.5, 3, 4, 5, 6, 7, and 8 hours after the initial dose on Day 1 or until the time of re-medication. The area between 2 consecutive time points was calculated as ([time 2−time 1]×[pain intensity difference at time 2 +pain intensity difference at time 1])/2.

Mean SPID at 8 hours post-dose was statistically significantly (p<0.0001) greater in the DPSGC25 mg group compared to the placebo group (11.67 vs. 4.06). Results were similar in the evaluable population Table 9.

A summary of SPID scores at 8 hours post initial dose of study drug for the full analysis and evaluable populations is presented in Table 9.

TABLE 9

SPID Scores at 8 Hours
Post Initial Dose of Study Drug (Full
Analysis and Evaluable Populations)

|  | Placebo | DPSGC 25 mg | p-value$_a$ |
|---|---|---|---|
| Full Analysis Population | (N = 99) | (N = 102) | <0.0001 |
| Mean (SD) | 4.06 (7.286) | 11.67 (14.302) | |
| Median | 0.86 | 3.28 | |
| Min-Max | −2.99-38.72 | −5.24-50.69 | |
| LS-mean | 3.83 | 11.40 | |
| Difference in LS-means | | −7.57 | |
| 95% CI for difference in LS-means | | −10.75, −4.38 | |
| Evaluable Population | (N = 95) | (N = 96) | <0.0001 |
| Mean (SD) | 4.20 (7.404) | 12.32 (14.457) | |
| Median | 0.86 | 4.58 | |
| Min-Max | −2.99-38.72 | −2.33-50.69 | |
| LS-mean | 3.96 | 12.12 | |

TABLE 9-continued

SPID Scores at 8 Hours
Post Initial Dose of Study Drug (Full
Analysis and Evaluable Populations)

|  | Placebo | DPSGC 25 mg | p-value$_a$ |
|---|---|---|---|
| Difference in LS-means |  | −8.16 |  |
| 95% CI for difference in LS-means |  | −11.45, −4.87 |  |

SD = standard deviation;
Min = minimum;
Max = maximum;
LS-mean = least squares mean
$_a$From 2-way ANOVA with factors for treatment and site.

During the initial dosing period, mean pain intensity scores were statistically significantly lower in the DPSGC 25 mg group compared to the placebo group at 1 hour (p=0.0470) and from 2 hours through 8 hours post-dose (p-values ranging from 0.0001 to 0.0091) using WOCF methodology. Results for PID and pain relief were consistent with those for pain intensity scores.

Results from the outpatient multiple dose period followed a similar pattern to those observed in the inpatient 48-hour multiple dose and 8-hour initial dosing periods. After discharge on Day 3, a statistically significantly (p<0.0001) smaller proportion of subjects in the DPSGC 25 mg group compared to the placebo group used rescue medication on Day 3 (12.7% vs. 39.4%) and on Day 4 (9.8% vs. 38.4%).

A statistically significant (p<0.0001) difference between the treatment groups was observed for subject's global assessment of study medication at study completion. Greater percentages of subjects in the DPSGC 25 mg group compared to the placebo group assessed study drug as very good or excellent at study completion (79.4% vs. 33.3%). See Table 10. Results were similar in the evaluable population. No DPSGC 25 mg subjects and one (1.0%) placebo subject discontinued due to inadequate pain relief.

A summary of subject global assessment of study drug at study completion for the full analysis and evaluable populations is presented in Table 10.

TABLE 10

Subject Global Assessment of Study
Drug at Study Completion
(Full Analysis and Evaluable Populations)

|  | Placebo | DPSGC 25 mg | p-value$_a$ |
|---|---|---|---|
| Full Analysis Population | (N = 99) | (N = 102) |  |
| Assessment at Study Completion |  |  |  |
| Poor, n (%) | 29 (29.3%) | 5 (4.9%) |  |
| Fair, n (%) | 12 (12.1%) | 3 (2.9%) |  |
| Good, n (%) | 24 (24.2%) | 12 (11.8%) |  |
| Very Good, n (%) | 19 (19.2%) | 20 (19.6%) |  |
| Excellent, n (%) Mean Response | 14 (14.1%) 2.77 | 61 (59.8%) 4.28 | <0.0001 |
| Evaluable Population | (N = 95) | (N = 96) |  |
| Assessment at Study Completion |  |  |  |
| Poor, n (%) | 27 (28.4%) | 5 (5.2%) |  |
| Fair, n (%) | 12 (12.6%) | 3 (3.1%) |  |
| Good, n (%) | 23 (24.2%) | 11 (11.5%) |  |
| Very Good, n (%) | 19 (20.0%) | 18 (18.8%) |  |
| Excellent, n (%) Mean Response | 14 (14.7%) 2.80 | 59 (61.5%) 4.28 | <0.0001 |

SD = standard deviation;
Min = minimum;
Max = maximum;
CI = confidence interval
$_a$From Cochran-Mantel-Haenszel test with site as stratification factor.

Pain Intensity Over Time

Mean NPRS scores over time during the 48-hour multiple dose period are presented graphically in FIG. 1. These results show similar levels of pain intensity at baseline in both groups. At the start of the 48-hour multiple dose period, which follows the variable-length single-dose portion of the study, the groups are statistically significantly different at all measurement time points (p<0.0001) including the baseline of the 48-hour multiple dose period (pre-dose 2 pain intensity assessment). This is true for both the measures taken 3 hours following the dose and 6 hours following the dose (i.e., at the time of the next dose). The results at 3 hours post-dose indicate superior analgesic efficacy of DPSGC 25 mg, and the results at 6 hours post-dose indicate that the analgesia in the DPSGC 25 mg group lasts for the 6-hour dosing interval. Results were similar in the evaluable population.

No statistically significant difference was observed between the DPSGC 25 mg and placebo groups for the mean NPRS pain intensity score at baseline (6.89 and 7.29, respectively) FIG. 2 shows the mean PID scores over time. The maximum pain intensity improvement occurred in both treatment groups at 45-60 minutes. However, the maximum mean PID was considerably greater in the DPSGC 25 mg group compared to placebo. This level of difference between groups was apparent throughout the follow-up interval.

Mean PID increased in the placebo group during the first 45 minutes post-dose (0.44 to 1.40). Mean PID increased in the DPSGC 25 mg group during the first hour post-dose (0.24 to 2.07) and remained stable from 1-2 hours (2.07 to 2.02). The relative difference between the treatment groups was generally maintained for the rest of the 8-hour period.

At 2.5 hours post-dose (p=0.0474) and from 4 hours through 8 hours post-dose on Day 1, mean PID was statistically significantly higher in the DPSGC 25 mg group compared to the placebo group (with p-values ranging from 0.0057 to 0.0173). Mean PID scores over time are displayed graphically in FIG. 2.

Time to Onset of Perceptible and Meaningful Pain Relief

Following the first dose of study medication, subjects were instructed to stop a stopwatch when "you have perceptible pain relief, that is when the relief from pain was first noticeable to you," with similar instruction for reporting meaningful pain relief Subjects were allowed to re-medicate as needed, though they were encouraged to wait one hour before doing so. For these analyses, subjects were censored at the time of re-medication. This has the potential to confound the interpretation of the time-to-event analyses, as reporting of perceptible or meaningful pain relief is related to the need to re-medicate, and could constitute informed censoring. Since the number of placebo subjects re-medicating is greater than the number of DPSGC 25 mg subjects, these analyses are likely to be biased in favor of placebo.

Statistically significantly more subjects in the DPSGC 25 mg group than in the placebo group reported perceptible pain relief following the first dose of study medication: 82.4% vs. 69.7% (p=0.0380), Table 5. Median time to onset of perceptible pain relief (Kaplan-Meier product estimate) was 26.01 minutes in the DPSGC 25 mg group and 22.18 minutes in the placebo group. These median times to onset were not statistically significantly different (overlapping 95% CIs). Similarly, the analyses comparing the full time-to-event curves also found no differences between the groups (log rank p=0.2348 and Wald chi-square p=0.3571). This endpoint arguably is most likely to reflect placebo response of all of the endpoints, given that it reflects an early impression of pain relief, rather than significant and durable relief. The significant impact of placebo response in pain models is well-documented in the literature and has been reported for many years. As expected, a large number of subjects in both groups were censored at 1 hour due to re-medication, though the number was larger in the placebo group.

Statistically significantly more subjects in the DPSGC 25 mg group than in the placebo group experienced meaningful pain relief (56.9% vs. 35.4%) (p=0.0025), Table 5. The median time to onset of meaningful pain relief after dose 1 (Kaplan-Meier product estimate) was shorter in the DPSGC 25 mg group compared to the placebo group (70.22 vs. 106.30 minutes), Table 5. The extended time to meaningful pain relief in this model, where baseline pain is severe, could be attributed to the fact that larger changes in pain intensity are necessary to achieve similar degrees of pain relief than when baseline pain is moderate.25 The 95% CIs about the medians overlapped slightly (84.7-not calculable vs. 61.2-92.0 minutes), indicating that the difference between the medians was not statistically significant. However, both the log-rank test and the Wald chi-square from the Cox proportional hazards model, which evaluate the entire time-to curve rather than just the medians, indicate a significant difference between the DPSGC 25 mg and placebo groups in time to onset of meaningful pain relief (p=0.0080 for the log-rank test and p=0.0142 for the Wald chi-square). A summary of onset of perceptible and meaningful pain relief for the full analysis and the evaluable population is presented in Table 11.

TABLE 11

Time to Onset of Perceptible and Meaningful Pain Relief (Full Analysis and Evaluable Populations)

|  | Placebo | DPSGC 25 mg | Log-rank p-value$_a$ | Wald Chi-square p-value$_a$ |
|---|---|---|---|---|
| Full Analysis Population |  |  |  |  |
| Time to perceptible pain relief | (N = 99) | (N = 102) |  |  |
| Subjects with relief, n (%) | 69 (69.7%) | 84 (82.4%) |  |  |
| Mean (SD) | 20.1 (16.41) | 25.2 (19.43) |  |  |
| Median | 14.9 | 18.8 |  |  |
| Min-Max | 2-105 | 1-91 |  |  |
| Median time$_a$ | 22.18 | 26.01 |  |  |
| 95% CI of time$_a$ | 16.58-35.82 | 18.58-31.32 | 0.2348 | 0.3571 |
| Time to meaningful pain relief | (N = 99) | (N = 102) |  |  |
| Subjects with relief, n (%) | 35 (35.4%) | 58 (56.9%) |  |  |
| Mean (SD) | 50.7 (28.65) | 50.3 (32.14) |  |  |
| Median | 45.5 | 46.1 |  |  |
| Min-Max | 13-114 | 11-152 |  |  |
| Median time$_a$ | 106.30 | 70.22 |  |  |
| 95% CI of time$_a$ | 84.72-NC | 61.18-92.00 | 0.0080 | 0.0142 |
| Evaluable Population |  |  |  |  |
| Time to perceptible pain relief | (N = 95) | (N = 96) |  |  |
| Subjects with relief, n (%) | 67 (70.5%) | 79 (82.3%) |  |  |
| Mean (SD) | 20.5 (16.54) | 25.5 (19.57) |  |  |
| Median | 15.0 | 19.0 |  |  |
| Min-Max | 2-105 | 3-91 |  |  |
| Median time$_a$ | 22.18 | 26.01 |  |  |
| 95% CI of time$_a$ | 17.20-34.82 | 18.58-31.32 | 0.2833 | 0.4674 |
| Time to meaningful pain relief | (N = 95) | (N = 96) |  |  |
| Subjects with relief, n (%) | 34 (35.8%) | 56 (58.3%) |  |  |
| Mean (SD) | 50.8 (29.08) | 51.5 (32.08) |  |  |
| Median | 45.4 | 47.1 |  |  |
| Min-Max | 13-114 | 11-152 |  |  |
| Median time$_a$ | 106.30 | 70.22 |  |  |
| 95% CI of time$_a$ | 84.72-NC | 61.18-90.00 | 0.0058 | 0.0112 |

SD = standard deviation;
Min = minimum;
Max = maximum;
CI = confidence interval;
NC = not calculable
$_a$Estimated using Kaplan-Meier product limit estimates including all subjects in the given population.

It is noted that two of the sites did not cover the elapsed time display on the stopwatches used to measure the meaningful and the perceptible time to relief. All subjects at these sites were handled in this same manner. A homogeneity analysis between sites showed no significant differences. While this protocol deviation is noted, common methodology employs both.

Severity of Adverse Events:

Table 12 summarizes treatment-related adverse events experienced by either treatment group. The majority of the treatment-emergent adverse events experienced during the study were classified by the Investigator as mild or moderate in severity. One severe adverse event was experienced by one subject (1.0%) in the DPSGC 25 mg group. This subject had a severe event of vomiting that started on Day 1 and resolved the same day without sequelae. The event was considered by the Investigator to be possibly related to study drug.

Severe adverse events were experienced by 5 subjects (5.1%) in the placebo group and included headache (2 subjects), coccydynia (1 subject), vomiting (1 subject), and arthralgia (1 subject). A statistically significantly smaller proportion of subjects in the DPSGC 25 mg group (20.6%) experienced at least 1 treatment-emergent adverse event compared to the placebo group (44.4%). Additionally, statistically significantly smaller proportions of subjects in the DPSGC 25 mg group experienced nausea (7.8%) and pyrexia (0%) compared to subjects in the placebo group (18.2% and 8.1%, respectively). The significantly greater incidence of nausea observed in the placebo group compared with the DPSGC 25 mg group is most likely related to inadequate pain relief or associated with the use of rescue medication. The significantly greater incidence of pyrexia, as well as body temperature increased, observed in the placebo group compared with the absence of pyrexia noted in the DPSGC 25 mg group is a result of the known antipyretic effect of NSAIDs.

No statistically significant differences were observed between the treatment groups for the overall incidence of treatment-related adverse events. Additionally, no statistically significant differences were observed between the treatment groups for the incidence of any specific treatment-related adverse event.

TABLE 12

Treatment-Related Adverse Events Experienced by ≧2% of Subjects in Either Treatment Group

| | Treatment Group n (%) | | | |
|---|---|---|---|---|
| | Placebo (N = 99) | (N = 102) | p-value$^a$ | DPSGC 25 mg |
| Number of Subjects with Any Event | 15 (15.2%) | 14 (13.7%) | 0.8422 | |
| Gastrointestinal Disorders | 13 (13.1%) | 12 (11.8%) | 0.8326 | |
| Abdominal Pain Constipation | 2 (2.0%) | 2 (2.0%) | 1.0000 | |
| | 1 (1.0%) | 3 (2.9%) | 0.6214 | |
| Diarrhoea | 0 | 2 (2.0%) | 0.4976 | |
| Nausea | 9 (9.1%) | 7 (6.9%) | 0.6102 | |
| Vomiting | 5 (5.1%) | 4 (3.9%) | 0.7452 | |
| Investigations | 2 (2.0%) | 0 | 0.2413 | |
| Body Temperature Increased | 2 (2.0%) | 0 | 0.2413 | |
| Nervous System Disorders | 3 (3.0%) | 3 (2.9%) | 1.0000 | |
| Headache | 2 (2.0%) | 3 (2.9%) | 1.0000 | |
| Skin and Subcutaneous Tissue Disorders | 2 (2.0%) | 2 (2.0%) | 1.0000 | |
| Pruritus | 2 (2.0%) | 2 (2.0%) | 1.0000 | |

The present invention is not limited in scope by the specific embodiments described. Modifications of the invention in addition to those described herein will become apparent to those skilled in the art from the foregoing description and the following claims.

What is claimed is:

1. A method of treating acute post-bunionectomy pain in a patient in need of such treatment, said method comprising orally administering to the patient a dose of between about 13 to about 30 mg of diclofenac potassium in a dispersible liquid formulation about every 4 hours to about 8 hours over a period of at least 24 hours, wherein the daily total amount of diclofenac potassium administered is less than or equal to about 100 mg.

2. The method according to claim 1, wherein internal fixation is performed during bunionectomy.

3. The method according to claim 1, wherein the diclofenac potassium in the dispersible liquid formulation is administered about every 5 hours to about 8 hours.

4. The method according to claim 1, wherein the diclofenac potassium in the dispersible liquid formulation is administered about every 6 hours.

5. The method according to claim 1, wherein the diclofenac potassium in the dispersible liquid formulation is administered over a period of at least about 30 hours.

6. The method according to claim 1, wherein the diclofenac potassium in the dispersible liquid formulation is administered over a period of at least about 48 hours, 72 hours, 96 hours, 120 hours, 144 hours, 168 hours or seven days.

7. The method according to claim 1, wherein the amount of the diclofenac potassium in the dispersible liquid formulation comprises at least about 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 22.5 mg, 25 mg, 27.5 mg, 28 mg, or 30 mg of diclofenac potassium.

8. The method according to claim 1, wherein the administered amount of diclofenac potassium in the dispersible liquid formulation is effective for treating acute pain for about 6 to about 8 hours after administration.

9. The method according to claim 1, wherein the plasma concentration of diclofenac in a patient ranges between about 670 to about 1500 ng/ml in less than about 30 minutes with the concomitant onset of relief of acute pain.

10. The method according to claim 1, wherein the administration of diclofenac potassium in the dispersible liquid formulation results in immediate increase in plasma concentration of diclofenac characterized by T(max) of about 0.47 hours.

11. The method according to claim 1, wherein diclofenac is substantially eliminated from plasma in the first 2 hours following administration.

12. The method according to claim 1, wherein the amount of the diclofenac potassium in the dispersible liquid formulation comprises about 25 mg of diclofenac potassium.

13. The method according to claim 12, wherein the administration of diclofenac potassium in the dispersible liquid formulation results in an average 48 hour NPRS pain score of about 2.49.

14. The method according to claim 12, wherein the administration of diclofenac potassium in the dispersible liquid formulation results in a median time to onset of greater than or equal to 30% pain reduction of about 60 minutes in an 8 hour initial dosing period.

15. The method according to claim 12, wherein the administration of diclofenac potassium in the dispersible liquid formulation provides a median time to onset of meaningful pain relief of about 70 minutes in an 8 hour initial dosing period.

16. The method according to claim 12, wherein the administration of diclofenac potassium in the dispersible liquid formulation provides clinically significant analgesic efficacy for about 6 hours.

17. The method according to claim 12, wherein 25 mg of diclofenac potassium in the dispersible liquid formulation is administered four times over a period of about 24 hours.

18. The method according to claim 1, wherein the diclofenac potassium in the dispersible liquid formulation is contained in a capsule.

19. The method according to claim 1, wherein the intensity of the acute pain is mild to moderate, moderate to moderately severe, or moderate to severe.

20. The method according to claim 1, wherein no opioid is co-administered with the diclofenac potassium in the dispersible liquid formulation.

* * * * *